United States Patent
Dubois et al.

(10) Patent No.: US 7,332,625 B2
(45) Date of Patent: Feb. 19, 2008

(54) PROCESS FOR THE PRODUCTION OF ACRYLIC ACID FROM PROPANE

(75) Inventors: Jean-Luc Dubois, Millery (FR); Fabienne Desdevises, Millery (FR); Stéphanie Serreau, Oullins (FR); Damien Vitry, Richebourg (FR); Wataru Ueda, Tokyo (JP)

(73) Assignee: Arkema, Puteaux (FR)

( * ) Notice: Subject to any disclaimer, the term of this patent is extended or adjusted under 35 U.S.C. 154(b) by 48 days.

(21) Appl. No.: 10/526,879

(22) PCT Filed: Sep. 9, 2003

(86) PCT No.: PCT/FR03/02673

§ 371 (c)(1),
(2), (4) Date: Oct. 28, 2005

(87) PCT Pub. No.: WO2004/024665

PCT Pub. Date: Mar. 25, 2004

(65) Prior Publication Data
US 2006/0183941 A1    Aug. 17, 2006

(30) Foreign Application Priority Data
Sep. 10, 2002  (FR)  ................................ 02 11197
May 27, 2003  (FR)  ................................ 03 06413

(51) Int. Cl.
*C07C 51/16* (2006.01)
(52) U.S. Cl. .................................................. 562/549
(58) Field of Classification Search ................ 562/523, 562/542, 549, 598

See application file for complete search history.

(56) References Cited

U.S. PATENT DOCUMENTS

| 6,291,393 | B1 | 9/2001 | Tu et al. | |
| 2002/0115879 | A1 | 8/2002 | Hinago et al. | |
| 2003/0017944 | A1 | 1/2003 | Hinago et al. | |
| 2003/0088124 | A1* | 5/2003 | Dubois | 562/547 |
| 2003/0187298 | A1* | 10/2003 | Borgmeier et al. | 562/546 |
| 2005/0054880 | A1* | 3/2005 | Dubois et al. | 562/547 |

FOREIGN PATENT DOCUMENTS

| DE | 101 45 958 A1 | 5/2002 |
| EP | 0 608 838 A2 | 8/1994 |
| EP | 0 895 809 A1 | 2/1999 |
| EP | 1 238 960 A1 | 9/2002 |
| FR | 2 833 005 A1 | 6/2003 |
| JP | 2000-256257 A | 9/2000 |

* cited by examiner

OTHER PUBLICATIONS

*French Search Report dated Mar. 4, 2004.

*Primary Examiner*—Karl Puttlitz
(74) *Attorney, Agent, or Firm*—Buchanan Ingersoll & Rooney PC

(57) ABSTRACT

The invention concerns a method for producing acrylic acid from propane, which consists in passing a gas mixture including propane, water, vapor, and optionally an inert gas and/or molecular oxygen, on a catalyst of formula (I): $Mo_1V_aSb_bNb_cSi_dO_x$, wherein: a ranges between 0.006 and 1, inclusively; b ranges between 0.006 and 1, inclusively; c ranges between 0.006 and 1, inclusively; d ranges between 0 and 3.5, inclusively; and x is the amount of oxygen bound to the other elements and depends on their state of oxidation, for oxidizing propane into acrylic acid, and which is carried out in the presence of molecular oxygen, the propane/molecular oxygen mol ratio in the initial gas mixture is not less than 0.5.

36 Claims, 2 Drawing Sheets

PROCESS FOR THE PRODUCTION OF ACRYLIC ACID FROM PROPANE

The present invention relates to the production of acrylic acid from propane in the presence or in the absence of molecular oxygen.

It is known from European patent application No. EP-A-608838 to prepare an unsaturated carboxylic acid from an alkane with a catalytic oxidation reaction, in vapor phase, in the presence of a catalyst containing a mixed metal oxide comprising as essential components, Mo, V, Te, O, as well as at least one element chosen from the group constituted by niobium, tantalum, tungsten, titanium, aluminium, zirconium, chromium, manganese, iron, ruthenium, cobalt, rhodium, nickel, palladium, platinum, antimony, bismuth, boron, indium and cerium, these elements being present in very precise proportions. The reaction can be implemented using a gaseous mixture composed of the alkane, oxygen, an inert gas and water vapor presenting the following molar proportions:

alkane/oxygen/inert gas/water vapor=1/0.1-10/0-20/0.2-70 and preferably 1/1-5/0-10/5-40.

Moreover, European patent application No. EP-A-895809 describes catalysts based on oxides comprising molybdenum, vanadium, niobium, oxygen, tellurium and/or antimony, as well as at least one other element such as iron or aluminium. These catalysts can be used for the conversion of propane to acrylic acid, in the presence of molecular oxygen, as illustrated in Examples 9 and 10. Example 9, in particular, describes the oxidation of propane using a catalyst having the formula

$Mo_1V_{0.33}Nb_{0.11}Te_{0.22}O_n$ from a gas flow composed of propane, oxygen, helium and a flow of water vapor, according to a molar ratio propane/oxygen/helium/water vapor of approximately 1/3.2/12.1/14.3. In such a gas flow, the flow of reactive gas has a very low concentration of propane. Consequently the recycling of the unconverted propane is much more difficult because this unconverted propane is too diluted in the reaction flow.

The aim of the invention is to propose a process for the production of acrylic acid from propane, in the presence or in the absence of molecular oxygen, which allows a higher conversion of propane to be obtained while retaining good acrylic acid selectivity.

The inventors have discovered that this aim can be achieved by passing a gaseous mixture comprising propane, water vapor, as well as optionally an inert gas and/or molecular oxygen, over a particular catalyst. When operating in the presence of molecular oxygen the oxidation is carried out under conditions such that the oxygen of the gaseous mixture is in a substoichiometric proportion in relation to the propane introduced, which probably allows the catalyst to act in a similar way to a redox system and provides the oxygen which is lacking so that the reaction is carried out in a satisfactory way.

The advantages of this novel process are the following:—
the limitation of the overoxidation of the products formed which takes place in the presence of too great a quantity of molecular oxygen; according to the present invention, due to the fact of operating in substoichiometry, the formation of $CO_x$ (carbon monoxide and carbon dioxide), degradation products, is reduced, which allows the acrylic acid selectivity to be increased;
the acrylic acid selectivity is maintained at a good level;
the conversion is increased without loss of selectivity;
the catalyst undergoes only a low reduction and therefore a small loss of its activity; it can easily be regenerated by heating in the presence of oxygen or a gas containing oxygen after a certain period of use; after regeneration, the catalyst regains its initial activity and can be used in another reaction cycle;
moreover, the separation of the stages of reduction of the catalyst and of regeneration of the latter can be provided which allows the partial pressure of propane to be increased, such a partial supply pressure of propane being little limited by the existence of an explosive zone created by the propane+oxygen mixture, because the later is present in molecular form in substoichiometric proportions;
moreover, this process allows reduction of the formation of products produced by hydration, in particular propionic acid, acetone and acetic acid.

The subject of the present invention is therefore a process for the production of acrylic acid from propane, in which a gaseous mixture containing propane, water vapor, optionally an inert gas, and/or molecular oxygen is passed over a catalyst of formula (I):

$$Mo_1V_aSb_bNb_cSi_dO_x \qquad (I)$$

in which:
a is comprised between 0.006 and 1, inclusive;
b is comprised between 0.006 and 1, inclusive;
c is comprised between 0.006 and 1, inclusive;
d is comprised between 0 and 3.5, inclusive; and
x is the quantity of oxygen bound to'the other elements and depends on their oxidation state.

in order to oxidize the propane to acrylic acid, and when operating in the presence of molecular oxygen, the molar ratio propane/molecular oxygen in the initial gaseous mixture is greater than 0.5.

Such a process allows an acrylic acid selectivity of close to 60% and a high conversion of propane to be obtained simultaneously. Moreover, it can easily be implemented in a fluidized bed or in a moving bed and the injection of the reagents can be carried out at different points of the reactor, so as to be outside of the flammability zone while having a high propane concentration and, consequently, a high catalyst productivity.

According to a particularly advantageous embodiment, the process according to the invention comprises the following stages:

I/ In the Absence of Molecular Oxygen

When the initial gaseous mixture is devoid of molecular oxygen, the propane is oxidized according to the following redox reaction (A):

$$SOLID_{oxidized} + PROPANE \rightarrow SOLID_{reduced} + ACRYLIC\ ACID \qquad (A)$$

II/ In the Presence of Molecular Oxygen
a) the initial gaseous mixture is introduced into a first reactor with a moving catalyst bed,
b) at the outlet of the first reactor, the gases are separated from the catalyst;
c) the catalyst is returned into a regenerator;
d) optionally the gases are introduced into a second reactor with a moving catalyst bed;
e) if appropriate, at the outlet of the second reactor, the gases are separated from the catalyst and the acrylic acid contained in the separated gases is recovered;

f) if appropriate, the catalyst is returned into the regenerator; and g) the regenerated catalyst from the regenerator is reintroduced into the first reactor and, if appropriate, the second reactor;

According to another advantageous embodiment of the invention, the reactor or reactors are also provided with a cocatalyst.

According to another advantageous embodiment of the invention, the process comprises the repetition, in a reactor provided with the catalyst of formula (I) and, if appropriate, with a cocatalyst, of the cycle comprising the following successive stages:

1) a stage of injection of the gaseous mixture as defined above;

2) a stage of injection of water vapor and, if appropriate, of inert gas;

3) a stage of injection of a mixture of molecular oxygen, water vapor and, if appropriate, inert gas; and 4) a stage of injection of water vapor and, if appropriate inert gas.

According to an improvement of the advantageous embodiment which has just been described, the cycle comprises an additional stage which precedes or follows stage 1) and during which a gaseous mixture corresponding to that of stage 1) is injected but without the molecular oxygen, the molar ratio propane/molecular oxygen then being calculated globally for stage 1) and this additional stage.

According to an advantageous embodiment of the improvement which has just been presented, the additional stage precedes stage 1) in the cycle.

Other characteristics and advantages of the invention will now be described in detail in the following description which is given with reference to the single attached figure which diagramatically represents an apparatus which is suitable for the implementation of an advantageous embodiment of the process according to the invention.

DETAILED DESCRIPTION OF THE INVENTION

Figure 1:
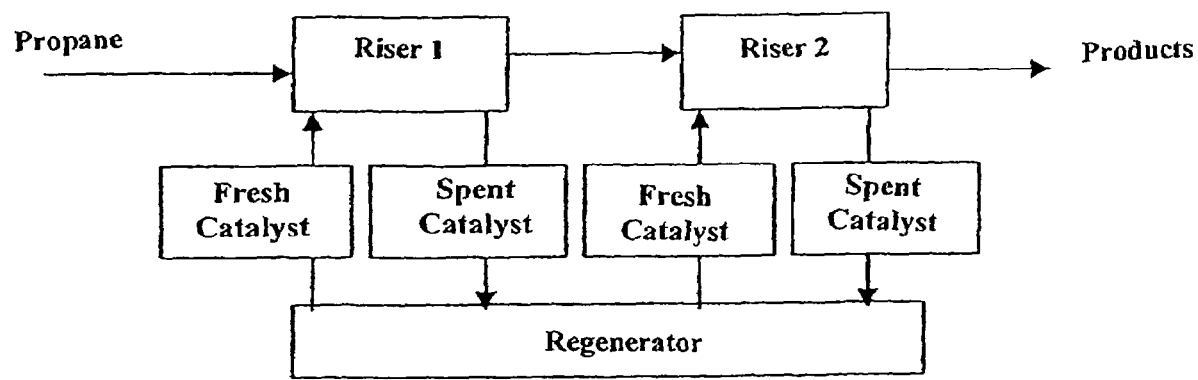
FIG. 1 is a simplified schematic representation of process steps according to an embodiment of the present invention.

According to the invention, in the alternatives where molecular oxygen is introduced, because the molar ratio propane/molecular oxygen in the initial gaseous mixture is greater than or equal to 0.5, the conversion of the propane to acrylic acid using the catalyst is carried out by oxidation, probably according to the following concurrent reactions (A) and (B):

the standard catalytic reaction (B):

$$CH_3\text{---}CH_2\text{---}CH_3 + 2O_2 \rightarrow CH_2\text{=}CH\text{---}COOH + 2H_2O \quad (B)$$

and the aforementioned redox reaction (A):

$$SOLID_{oxidized} + CH_3\text{---}CH_2\text{---}CH_3 \rightarrow SOLID_{reduced} + CH_2\text{=}CH\text{---}COOH \quad (A)$$

The propane/water vapor volume ratio in the initial gaseous mixture is not critical and can vary within wide limits.

Similarly, the proportion of inert gas, which can be helium, krypton, a mixture of these two gasses, or nitrogen, carbon dioxide, etc., is also not critical and can also vary within wide limits.

The proportions of the constituents of the initial gaseous mixture are generally as follows (in molar ratios):

propane/oxygen/inert(He—Kr)/$H_2O$ (vapor)=1/0.05-2/1-10/1-10

Preferably, they are 1/0.1-1/1-5/1-5.

Yet more preferably, they are 1/0.167-0.667/2-5/2-5. As particularly beneficial proportions the following may also be cited:

1/0.2-0.4/4-5/4-5.

Generally, reactions (A) and (B) are carried out at a temperature of 200 to 500° C., preferably from 250 to 450° C., yet more preferably from 350 to 400° C. The pressure in the reactor or reactors is generally from $1.01 \times 10^4$ to $1.01 \times 10^6$ Pa (0.1 to 10 atmospheres), preferably from $5.05 \times 10^4$ to $5.05 \times 10^5$ Pa (0.0-5 atmospheres).

The residence time in the reactor, or if there are several, in each reactor, is generally from 0.01 to 90 seconds, preferably from 0.1 to 30 seconds.

The catalyst corresponds to the following formula (I):

$$Mo_1V_aSb_bNb_cSi_dO_x \quad (I)$$

in which:

a is comprised between 0.006 and 1, inclusive;
b is comprised between 0.006 and 1, inclusive;
c is comprised between 0.006 and 1, inclusive;
d is comprised between 0 and 3.5, inclusive; and
x is the quantity of oxygen bound to the other elements and depends on their oxidation state.

Advantageously:

a is comprised between 0.09 and 0.8, inclusive;
b is comprised between 0.04 and 0.6, inclusive;
c is comprised between 0.01 and 0.4, inclusive; and
d is comprised between 0.4 and 1.6, inclusive.

The oxides of the different metals included in the composition of the catalyst of formula (I) can be used as raw materials in the preparation of this catalyst, but the raw materials are not limited to the oxides; among the raw materials which can be used there may be mentioned, as non-limitative examples:

in the case of molybdenum, ammonium molybdate, ammonium paramolybdate, ammonium heptamolybdate, molybdic acid, molybdenum halides or oxyhalides such as $MoCl_5$, organometallic compounds of molybdenum such as molybdenum alkoxides such as $Mo(OC_2H_5)_5$, acetylacetone molybdenyl;

in the case of vanadium, ammonium metavanadate, vanadium halides or oxyhalides such as $VCl_4$, $VCl_5$ or $VOCl_3$, organometallic compounds of vanadium such as vanadium alkoxides such as $VO(OC_2H_5)_3$;

in the case of antimony for example antimony oxide (antimony trioxide), in particular of the senarmontite variety, antimony trisulphate, $(Sb_2(SO_4)_3)$ or an antimony chloride (antimony trichloride, antimony pentachloride);

in the case of niobium, niobic acid, niobium tartrate, niobium hydrogen oxalate, oxotrioxalatoammonium niobate $\{(NH_4)_3[NbO(C_2O_4)_3]\cdot 1.5H_2O\}$, niobium and ammonium oxalate, niobium oxalate and tartrate, niobium halides or oxyhalides such as $NbCl_3$, $NbCl_5$ and organometallic compounds of niobium such as niobium alkoxides such as Nb(OC$_2$H$_5$)$_5$, Nb(O-n-Bu)$_5$;

and, generally, all the compounds which are able to form an oxide by calcination, namely, the metallic salts of organic acids, the metallic salts of mineral acids, the metal complex compounds, etc.

The source of silicon is generally constituted by colloidal silica and/or polysilicic acid.

According to particular embodiments, the catalyst of formula (I) can be prepared by mixing aqueous solutions of niobic acid, oxalic acid, ammonium heptamolybdate, ammonium metavanadate, antimony oxide, under stirring, by the addition, if appropriate, of colloidal silica, then by precalcinating under air at a temperature comprised between 280 and 340° C., preferably at approximately 300-320° C. and by calcinating under nitrogen at approximately 600° C.

Preferably, in the thus-prepared catalyst of formula (I):
a is comprised between 0.09 and 0.8, inclusive;
b is comprised between 0.04 and 0.6, inclusive;
c is comprised between 0.01 and 0.4, inclusive; and
d is comprised between 0.4 and 1.6, inclusive.

More particularly, the process for the preparation of the catalyst of formula (I) is implemented by the preparation of a solution of niobic acid, oxalic acid, preparation of a solution of molybdenum, vanadium, antimony and optionally silica, a mixture of the 2 solutions produces the formation of a gel, drying of the gel obtained produces the formation of a precursor of formula (I') below, precalcination then calcination.

More precisely, according to a particularly preferred process, the catalyst can be prepared by implementing the following stages:
1) dissolution in water of a source of vanadium, for example, ammonium metavanadate, under stirring and optionally by heating;
2) addition to the previously obtained solution of a source of antimony, for example antimony oxide in particular the senarmonite variety;
3) addition of a source of molybdenum, for example, ammonium heptamolybdate;
4) reaction of the solution obtained, under reflux;
5) addition of an oxidizing agent such as hydrogen peroxide;
6) if appropriate, addition of silica;
7) addition of a solution prepared by mixing, under heating, a source of niobium, for example, niobic acid, with oxalic acid;
8) reaction of the reaction mixture under reflux and preferably under inert atmosphere, until a gel is obtained;
drying of the gel obtained which leads to a precursor;
9) precalcination of the precursor; and
10) calcination of the precalcinated gel in order to obtain the catalyst.

As a variant, instead of having three successive stages 1), 2) and 3), these stages are combined by introducing the sources of vanadium, antimony and molybdenum into cold water and stirring in order to obtain a solution.

Preferably, in stage 5), hydrogen peroxide is added until an orange-coloured limpid solution is obtained.

In the alternative processs below:
the drying (for example of stage 9) can be carried out in an oven in a thin layer, by atomization, freeze-drying, zeodration, with microwaves, etc.
the precalcination can be carried out under air flow at 280-300° C. or under static air at 320° C., in a fluidized bed, in a rotary furnace in a so-called aerated fixed bed, so that the catalyst pellets are separated from each other in order to prevent them from fusing during precalcination or possibly during calcination;
the calcination is preferably carried out under very pure nitrogen and at a temperature close to 600° C., for example in a rotary furnace or in a fluidized bed and for a duration which can be 2 hours.

The catalyst obtained at the end of the calcination can be ground in order to produce smaller particles. If the grinding is continued until a powder constituted by particles of approximately the size of a micron is obtained, the powder can subsequently be returned to its form using a binding agent such as for example silica in the form of polysilicic acid, the suspension then being dried again, for example by atomization.

According to a more particularly preferred embodiment of the invention, the precalcination is carried out:
either at a temperature of less than 300° C. under an air flow of at least 10 ml/min/g of catalyst;
or at a temperature ranging from 300 to 350° C. under an air flow less than 10 ml/min/g of catalyst.

According to a particularly preferred embodiment, the precalcination is carried out:
at approximately 320° C. under an air flow less than 10 ml/min/g; or
at approximately 290° C. under an air flow of approximately 50 ml/min/g.

Regeneration of the Catalyst

During the redox reaction (B), the catalyst undergoes reduction and a progressive loss of its activity. This is why, once the catalyst has at least partially changed to the reduced state, its regeneration is carried out according to reaction (C):

$$SOLID_{reduced} + O_2 \rightarrow SOLID_{oxidized} \quad (C)$$

by heating in the presence of oxygen or a gas containing oxygen at a temperature of 250 to 500° C., for a time necessary for the reoxidation of the catalyst.

The proportions of the constituents of the regeneration gaseous mixture are generally as follows (in molar ratios):
oxygen/inert(He—Kr)H$_2$O(vapor)=1/1-10/0-10

Preferably, they are 1/1-5/0-5.

Instead of using the oxygen alone, dry air (21% O$_2$) can be used. Instead of or in addition to the water vapor, moist air can thus be used.

The regeneration temperature is generally from 250 to 500° C.

Generally the process is carried out until the reduction ratio of the catalyst is comprised between 0.1 and 10 g of oxygen per kg of catalyst.

This reduction ratio can be monitored during the reaction through the quantity of products obtained. Then the equivalent quantity of oxygen is calculated. It can also be monitored through the exothermicity of the reaction. The reduction ratio can also be monitored through the quantity of oxygen consumed in the regenerator.

After regeneration, which can be carried out under temperature and pressure conditions which are identical to, or different from those of the reactions (A) and (B), the catalyst regains an initial activity and can be reintroduced into the reactors.

The reactions (A) and (B) and the regeneration (C) can be carried out in a standard reactor, such as a fixed bed reactor, a fluidized bed reactor or a moving bed reactor.

Thus the reactions (A) and (B) and the regeneration (C) can be carried out in a device with two stages, namely a reactor and a regenerator which operate simultaneously and in which two catalyst loadings alternate periodically.

The reactions (A) and (B) and the regeneration (C) can also be carried out in the same reactor by alternating the periods of reaction and regeneration.

Preferably, the reactions (A) and (B) and the regeneration (C) are carried out in a reactor with a moving catalyst bed, in particular in a vertical reactor, the catalyst then preferably moving from the bottom upwards.

An operating process with only one passage of the gas or with recycling of the gas can be used.

According to a preferred embodiment, the propylene produced and/or the propane which has not reacted are recycled (or returned) to the inlet of the reactor, i.e. they are reintroduced at the inlet of the reactor, in a mixture or in parallel with the initial mixture of propane, water vapor and if appropriate inert gas or gases.

Use of an Apparatus with Two Reactors and a Regenerator

According to an advantageous embodiment of the invention, the process according to the invention is used in an apparatus such as the one represented in the attached figure.

The initial gaseous mixture comprising propane, molecular oxygen, water vapor as well as, if appropriate, an inert gas, is introduced into a first reactor (Riser 1) containing the moving catalyst bed.

Then, at the outlet of the first reactor, the effluents are separated into gases and the moving catalyst bed.

The catalyst is sent into a regenerator.

The gases are introduced into a second reactor (Riser 2) also containing a moving catalyst bed.

At the outlet of the second reactor, the effluents are separated into gases and the moving bed catalyst.

The catalyst is sent into a regenerator.

The gases are treated in a known way, generally by absorption and purification, with a view to recovering the acrylic acid produced.

The regenerated catalyst is reintroduced into the first reactor as well as into the second reactor.

The process thus operates continuously, the circulation of the catalyst between the reactors and the regenerator is carried out in a regular and generally continuous way.

Of course, the single regenerator can be replaced by two or more regenerators.

Moreover, it is possible to add, after the second reactor, other reactors which also have a catalyst circulating between each of these reactors and the regenerator or other regenerators.

Preferably, the first and second reactors are vertical and the catalyst is transported upwards by the gas flow.

An operating process with only one passage of gases or with recycling of the products leaving the second reactor can be used.

According to a preferred embodiment of the invention, after treatment of the gas originating from the second reactor, the propylene produced and/or the propane which has not reacted are recycled (or returned) to the inlet of the reactor, i.e. they are reintroduced at the inlet of the first reactor, in a mixture or in parallel with the initial mixture of propane, oxygen, water vapor and, if appropriate, inert gas or gases.

Use of a Cocatalyst

According to another advantageous embodiment of the invention, the gaseous mixture also passes over a cocatalyst.

This has the advantage of reducing the production of propionic acid, which is generally a by-product of the conversion reaction and which poses problems in certain applications of acrylic acid when it is present in too great a quantity.

Thus, the propionic acid/acrylic acid ratio is greatly reduced at the outlet of the reactor.

Moreover, the formation of acetone, which is also a by-product of the production of acrylic acid from propane, is reduced.

To this end, at least one of the reactors comprises a cocatalyst with the following formula (II):

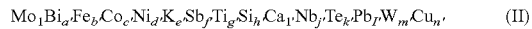

$$Mo_1Bi_{a'}Fe_{b'}Co_{c'}Ni_{d'}K_{e'}Sb_{f'}Ti_{g'}Si_{h'}Ca_{i'}Nb_{j'}Te_{k'}Pb_{l'}W_{m'}Cu_{n'}$$ (II)

in which:
a' is comprised between 0.006 and 1, inclusive;
b' is comprised between 0 and 3.5, inclusive;
c' is comprised between 0 and 3.5, inclusive;
d' is comprised between 0 and 3.5, inclusive;
e' is comprised between 0 and 1, inclusive;
f' is comprised between 0 and 1, inclusive;
g' is comprised between 0 and 1, inclusive;
h' is comprised between 0 and 3.5, inclusive;
i' is comprised between 0 and 1, inclusive;
j' is comprised between 0 and 1, inclusive;
k' is comprised between 0 and 1, inclusive;
l' is comprised between 0 and 1, inclusive;
m' is comprised between 0 and 1, inclusive; and
n' is comprised between 0 and 1, inclusive.

Such a cocatalyst can be prepared in the same way as the catalyst of formula (I).

The oxides of the different metals included in the composition of the cocatalyst of formula (II) can be used as raw materials in the preparation of this cocatalyst, but the raw materials are not limited to the oxides; as other raw materials, the corresponding nitrates can be mentioned in the case of nickel, cobalt, bismuth, iron or potassium.

Generally, the cocatalyst is present in the form of a moving bed and preferably it is regenerated and circulates, if appropriate, in the same way as the catalyst.

Preferably, in the cocatalyst of formula (II):
a' is comprised between 0.01 and 0.4, inclusive;
b' is comprised between 0.2 and 1.6, inclusive;
c' is comprised between 0.3 and 1.6, inclusive;
d' is comprised between 0.1 and 0.6, inclusive;
e' is comprised between 0.006 and 0.01, inclusive.
f' is comprised between 0 and 0.4, inclusive;
g' is comprised between 0 and 0.4, inclusive;
h' is comprised between 0.01 and 1.6, inclusive;
i' is comprised between 0 and 0.4, inclusive;
j' is comprised between 0 and 0.4, inclusive;
k' is comprised between 0 and 0.4, inclusive;
l' is comprised between 0 and 0.4, inclusive;
m' is comprised between 0 and 0.4, inclusive; and
n' is comprised between 0 and 0.4, inclusive.

The weight ratio of the catalyst to the cocatalyst is generally greater than 0.5 and preferably at least 1.

Advantageously, the cocatalyst is present in the two reactors.

The catalyst and the cocatalyst are present in the form of solid catalytic compositions.

They can each be in the form of pellets, generally of 20 to 300 µm in diameter, the catalyst and cocatalyst pellets generally being mixed before implementation of the process according to the invention.

The catalyst and the cocatalyst can also be present in the form of a solid catalytic composition composed of pellets each of which comprises both the catalyst and the cocatalyst.

EXAMPLES

The following examples illustrate the present invention without limiting its scope.

In the formulae given in Example 1, x is the quantity of oxygen bound to the other elements and depends on their oxidation states.

The conversions, selectivities and yields are defined as follows $$\text{Conversion (\%) of the propane} = \frac{\text{Number of moles of propane having reacted}}{\text{Number of moles of propane introduced}} \times 100$$

$$\text{Selectivity (\%) for acrylic acid} = \frac{\text{Number of moles of acrylic acid formed}}{\text{Number of moles of propane having reacted}} \times 100$$

$$\text{Yield (\%) of acrylic acid} = \frac{\text{Number of moles of acrylic acid formed}}{\text{Number of moles of propane introduced}} \times 100$$

The selectivities and yields relating to the other compounds are calculated in a similar way.

The conversion ratio is the weight of catalyst (in kg) required to convert 1 kg of propane.

Example 1 (comparative)

A catalyst was prepared in the following way.

5.35 g of ammonium paramolybdate and 1.33 g of antimony trisulphate ($Sb_2(SO_4)_3$) are successively added under stirring to 30 ml of water heated to 80° C. Stirring is continued for 15 minutes. Separately, a solution containing 10 mmoles of vanadium is prepared by dissolving 2.63 g of hydrated vanadyl sulphate in 10 ml of distilled water heated to 80° C. The second solution is added to the first and the mixture is stirred for 15 minutes before being introduced into a 70 ml autoclave covered with Teflon®. Then nitrogen is bubbled through for 5 minutes so that it substitutes the air present in the autoclave, before it is closed. The autoclave is then set at 175° C. for 24 hours. After this period, the autoclave is cooled down with tap water for 10 minutes. The black-purple solid obtained in the autoclave is separated from the solution by filtration, thoroughly washed with distilled water and dried for 12 hours at 80° C. The precursor thus obtained is then precalcinated under air at 280° C. for 2 hours, then calcinated under nitrogen flow (25 ml/h/g) at 600° C. for 2 hours. In this way catalyst 1 is obtained. This catalyst is tested. The results are shown in Tables 2 and 3.

Example 2 (comparative)

A catalyst was prepared in the following way.

5.35 g of ammonium paramolybdate and 0.55 g of a 31% solution of hydrogen peroxide and 0.74 g of antimony trioxide are successively added to 20 ml of water heated to 80° C. under stirring. Stirring is continued for 60 minutes until the antimony oxide is dissolved. Separately, a solution containing 12 mmoles of vanadium is prepared by dissolving 3.16 g of hydrated vanadyl sulphate in 10 ml of distilled water heated to 80° C. The second solution is added to the first and 1.89 g of oxalic acid in powder form is added to the solution. The mixture is stirred for 10 minutes before being introduced into a 70 ml autoclave covered with Teflon®. Then nitrogen is bubbled through for 5 minutes so that it substitutes the air present in the autoclave, before the latter is closed. The autoclave is then set at 175° C. for 48 hours.

After this period, the autoclave is cooled down with tap water for 10 minutes. The black-purple solid obtained in the autoclave is separated from the solution by filtration, thoroughly washed with distilled water and dried for 12 hours at 80° C. The precursor thus obtained is then calcinated under nitrogen flow (25 ml/h/g) at 600° C. for 2 hours. In this way catalyst 2 is obtained. This catalyst is tested. The results are shown in Tables 2 and 3.

Example 3

A catalyst was prepared in the following way.

5.35 g of ammonium paramolybdate and 0.55 g of a 31% solution of hydrogen peroxide and 0.74 g of antimony trioxide are successively added to 20 ml of water heated to 80° C. under stirring. Stirring is continued for 60 minutes until the antimony oxide is dissolved. Separately, a solution containing 9 mmoles of vanadium is prepared by dissolving 2.37 g of hydrated vanadyl sulphate in 10 ml of distilled water heated to 80° C. A third solution containing 3 mmoles of niobium is prepared simultaneously by dissolving under stirring, 1.94 g of hydrated niobium oxalate in 10 ml of distilled water heated to 80° C. The second solution is added to the first and stirred continuously for 5 minutes. Finally, the solution containing niobium is added. The mixture is stirred for 10 minutes before being introduced into a 70 ml autoclave covered with Teflon®. Then nitrogen is bubbled through for 5 minutes so that it substitutes the air present in the autoclave, before the latter is closed. The autoclave is then set at 175° C. for 48 hours.

After this period, the autoclave is cooled down with tap water for 10 minutes. The black-purple solid obtained in the autoclave is separated from the solution by filtration, thoroughly washed with distilled water and dried for 12 hours at 80° C. The precursor thus obtained is then calcinated under nitrogen flow (25 ml/h/g) at 600° C. for 2 hours. In this way catalyst 3 is obtained. This catalyst is tested under the same conditions as the other catalysts. The results are shown in Tables 2 and 3.

Example 4

A catalyst was prepared in the following way.

5.35 g of ammonium paramolybdate and 0.55 g of a 31% solution of hydrogen peroxide and 0.74 g of antimony trioxide are successively added to 20 ml of water heated to 80° C. under stirring. Stirring is continued for 60 minutes until the antimony oxide is dissolved. Separately, a solution containing 12 mmoles of vanadium is prepared by dissolving 3.16 g of hydrated vanadyl sulphate in 10 ml of distilled water heated to 80° C. A third solution containing 1.5 mmoles of niobium is simultaneously prepared by dissolving under stirring, 0.97 g of hydrated niobium oxalate in 10 ml of distilled water heated to 80° C. The second solution is added to the first and stirred continuously for 5 minutes. Finally, the solution containing niobium is added. The mixture is stirred for 10 minutes before being introduced into a 70 ml autoclave covered with Teflon®. Then nitrogen is bubbled through for 5 minutes so that it substitutes the air present in the autoclave, before the latter is closed. The autoclave is then set at 175° C. for 48 hours.

After this period, the autoclave is cooled down with tap water for 10 minutes. The black-purple solid obtained in the autoclave is separated from the solution by filtration, thoroughly washed with distilled water and dried for 12 hours at 80° C. The precursor thus obtained is then calcinated under nitrogen flow (25 ml/h/g) at 600° C. for 2 hours. In this way catalyst 4 is obtained. This catalyst is tested under the same conditions as catalyst 3. The results are shown in Tables 2 and 3.

Example 5 (comparative)

A catalyst was prepared in the following way.

2.0008 g of hot (90° C.) ammonium metavanadate is dissolved in 45 ml of water. Then 1.2149 g of antimony trioxide (senarmontite phase) and 10.0142 g of ammonium heptamolybdate are added. The mixture is taken to reflux under argon, the temperature is set at 70° C. and the solution is left under stirring for 14 hours. The resulting mixture is opaque blue-black. 2 ml of 30% hydrogen peroxide is added using a syringe and the solution is left under stirring. The colour progressively changes to orange passing through khaki green tones. A light precipitate is then distinguished in a dark orange solution. In parallel, 1.7254 g of oxalic acid was dissolved in 20 ml of water and this solution is added to the first, which remained at 70° C., without a change of colour or appearance being observed. The pH of the solution is then 3 to 4. The mixture is left to mature for another 30 minutes, then it is dried in the oven for 12 hours at 110° C. The amorphous precursor is then precalcinated under air (15 ml/min/g) at 300° C., for 4 hours, then calcinated under nitrogen flow (15 ml/min/g) for 2 hours at 600° C. In this way catalyst 5 is obtained. This catalyst is tested under the same conditions as the other catalysts. The results are shown in Table 4.

Example 6

Catalyst 6 is prepared in the same way as catalyst 5, except that 0.75 g of niobic acid is dissolved in the oxalic acid solution, by heating it at 70° C. for 2 hours. This solution is centrifuged before being mixed with the solution containing the other elements. The results are shown in Table 4.

Example 7

A catalyst was prepared in the following way.

5.35 g of ammonium paramolybdate is added under stirring to 20 ml of water heated to 80° C. Separately, a solution containing 15 mmoles of vanadium is prepared by dissolving 3.94 g of hydrated vanadyl sulphate in 20 ml of distilled water heated to 80° C. The second solution is added to the first and the mixture is then stirred for 10 minutes before being introduced into a 70 ml autoclave covered with Teflon®. Then nitrogen is bubbled through for 5 minutes so that it substitutes the air present in the autoclave, before the latter is closed. The autoclave is then set at 175° C. for 24 hours.

After this period, the autoclave is cooled down with tap water for 10 minutes. The black-blue solid obtained in the autoclave is separated from the solution by filtration, thoroughly washed with distilled water and dried for 12 hours at 80° C. The precursor thus obtained is then calcinated under nitrogen flow (25 ml/h/g) at 500° C. for 2 hours. In this way catalyst 7 is obtained. This catalyst is tested under the same conditions as the other catalysts.

TABLE 1

Summary table of the different preparations

| Example No. | Composition of the solution (without oxygen) | Process of preparation |
|---|---|---|
| Example 1 | $Mo_{1.0}V_{0.33}Te_{0.17}$ | Hydrothermal synthesis |
| Example 2 | $Mo_{1.0}V_{0.40}Sb_{0.17}$ | Hydrothermal synthesis |
| Example 3 | $Mo_{1.0}V_{0.30}Sb_{0.17}Nb_{0.10}$ | Hydrothermal synthesis |
| Example 4 | $Mo_{1.0}V_{0.40}Sb_{0.17}Nb_{0.05}$ | Hydrothermal synthesis |
| Example 5 | $Mo_{1.0}V_{0.30}Sb_{0.15}$ | Evaporation drying |
| Example 6 | $Mo_{1.0}V_{0.30}Sb_{0.15}Nb_{0.08}$ | Evaporation drying |
| Example 7 | $Mo_{0.1}V_{0.50}$ | Hydrothermal synthesis |

TABLE 2

Oxidation of propane at 320° C. on antimony catalysts

| Ex. No. | Conversion (%) $C_3H_8$ | Selectivity (%) Acrylic acid | $C_3H_6$ | Acetone | Acetic acid | CO | $CO_2$ | Yield (%) Acrylic acid |
|---|---|---|---|---|---|---|---|---|
| 1 | 9.74 | 34.3 | 19.6 | 5.88 | 17.0 | 14.0 | 9.25 | 3.34 |
| 2 | 13.1 | 12.1 | 19.3 | 2.05 | 23.5 | 21.1 | 21.9 | 1.59 |
| 3 | 10.2 | 44.1 | 26.9 | 3.45 | 10.3 | 7.89 | 7.33 | 4.50 |
| 4 | 21.6 | 40.0 | 15.0 | 2.00 | 16.0 | 13.0 | 13.0 | 8.64 |
| 7 | 11.1 | 5.41 | 19.5 | 0.97 | 20.4 | 33.1 | 20.6 | 0.60 |

TABLE 3

Oxidation of propane at 360° C. on antimony catalysts

| Ex. No. | Conversion (%) $C_3H_8$ | Selectivity (%) Acrylic acid | $C_3H_6$ | Acetone | Acetic acid | CO | $CO_2$ | Yield (%) Acrylic acid |
|---|---|---|---|---|---|---|---|---|
| 1 | 20.8 | 33.9 | 15.3 | 1.70 | 17.5 | 17.6 | 14.0 | 7.05 |
| 2 | 21.9 | 11.0 | 14.7 | 1.23 | 22.8 | 24.7 | 25.5 | 2.41 |
| 3 | 21.2 | 45.1 | 17.7 | 1.07 | 11.8 | 13.1 | 11.3 | 9.56 |
| 4 | 37.8 | 19.0 | 8.0 | 1.00 | 21.0 | 24.0 | 27.0 | 7.18 |
| 7 | 23.4 | 4.21 | 11.4 | 0.27 | 14.8 | 41.4 | 27.9 | 0.98 |

TABLE 4

Oxidation of propane on the evaporation-drying catalysts

| Ex. No. | Reaction temp. ° C. | Conv. % $C_3H_8$ | Selectivity (%) Acrylic acid | $C_3H_6$ | Acetone | Acetic acid | CO | $CO_2$ | Yield (%) Acrylic acid |
|---|---|---|---|---|---|---|---|---|---|
| 5 | 320 | 9.76 | 27.1 | 30.2 | 5.20 | 13.0 | 13.4 | 11.1 | 2.33 |
| 6 | 320 | 7.21 | 24.0 | 35.7 | 2.91 | 13.4 | 13.3 | 10.7 | 1.73 |

TABLE 4-continued

Oxidation of propane on the evaporation-drying catalysts

| Ex. No. | Reaction temp. °C. | Conv. % $C_3H_8$ | Selectivity (%) | | | | | | Yield (%) Acrylic acid |
|---|---|---|---|---|---|---|---|---|---|
| | | | Acrylic acid | $C_3H_6$ | Acetone | Acetic acid | CO | $CO_2$ | |
| 5 | 360 | 15.6 | 29.4 | 19.8 | 1.77 | 15.2 | 17.8 | 16.0 | 5.06 |
| 6 | 360 | 23.8 | 25.1 | 18.7 | 0.59 | 11.9 | 23.9 | 19.9 | 5.96 |

In the case of examples 1 and 3, the effluents of the test are collected for 4 hours in an ice-trap. 2 analyses by chromatography coupled with a mass spectrometer are carried out per sample.

5 main products are detected per sample: acetone, water, acetic acid, propionic acid and acrylic acid.

The molar ratios propionic acid/acrylic acid are thus calculated for each sample, for reaction temperatures of 320° C. and 360° C. The average of the two analyses carried out per sample is given in Table 5 below.

TABLE 5

Molar ratio Propionic acid/Acrylic acid

| Example | 320° C. | 360° C. |
|---|---|---|
| 1 | 6.49% | 1.64% |
| 3 | 6.36% | 1.42% |

It is noted that the molar ratio decreases with an increase in the temperature and the presence of niobium in the composition of the catalyst.

Example 8

Preparation of a Catalyst A of Formula: $Mo_1V_{0.30}Sb_{0.15}Nb_{0.10}Si_{0.93}O_x$ and its Precursor.

Synthesis of the Precursor

This synthesis allows the preparation of approximately 100 g of dry precursor.

Stage 1: Dissolution-precipitation

Solution A 12.3 g (0.1052 mol V) of ammonium metavanadate (AMV) are placed in solution in 260 ml of demineralised water, in a 1 liter glass SVL® reactor, under stirring, in an oil bath thermostatically controlled at 128° C. A yellow solution is obtained. 7.7 g (0.0528 mol Sb) of $Sb_2O_3$ are added to the limpid solution (small addition of water in order to rinse the funnel), then 61.8 g of ammonium heptamolybdate (AHM, 0.3501 moles of Mo) are added. After the addition of AHM, the reactor is flushed with nitrogen, the reaction is stirred continuously, at reflux, for 4 hours. Gradually a blue-black solution is obtained.

Solution B 6 g (0.0530 mol) of an aqueous solution of $H_2O_2$ at 30 wt.-% is then added slowly (approximately 30 minutes). In order to obtain a limpid orange solution, two drops of pure oxygenated water are added.

Solution C

Then 49.1 g of Ludox® AS40 silica ($n_{Si}$=0.327 mole) is added in one go, and the solution becomes slightly cloudy. The solution formed is called solution C.

Solution D

A solution D is prepared at the same time as solution A. 100 g of distilled water, 5.9 g of niobic acid marketed by the Brazilian company CBMM i.e. $n_{Nb}$=0.035 mol, and 13.2 g of Prolabo oxalic acid i.e. $n_{Oxalate}$=0.105 mole is introduced into a 500 ml beaker. The mixture is heated at 60° C. under stirring for 2 hours, then taken to 30° C. The solution is then centrifuged at 6200 r.p.m. for 12 minutes in order to obtain a limpid solution.

Solution D is added to solution C in one go. A fluid gel is obtained which is orange then yellow. Stirring is continued for 30 minutes under nitrogen flow, under reflux.

Stage 2: Drying

The gel is then dried in a ventilated oven overnight, on plates covered with Teflon®, at 130° C. 86.3 g of dry precursor are recovered. The precursor is in the form of sheets, black on the top and a thin green film underneath. In this way a precursor is obtained.

Stage 3: Heat Treatment 30 g of precursor obtained previously are precalcinated at 305° C. with an air flow rate of 18.7 ml/min/g.

After calcination, at 601° C. under a nitrogen flow rate of 49.8 ml/min/g, a weight of calcinated solid of 24.6 g is obtained. This catalyst is called CATALYST A.

Example 9

Preparation of a Catalyst B with the Formula: $Mo_1V_{0.30}Sb_{0.15}Nb_{0.10}Si_{0.76}O_x$ and its Precursor.

Synthesis of the Precursor

The process is carried out as in Example 8, but with;

30.75 g (0.2630 mole of V) of ammonium metavanadate (MVA);

19.25 g (0.1321 mole of Sb) of $Sb_2O_3$;

154.5 g (0.8753 mole of Mo) of ammonium heptamolybdate (AHM);

15.25 g (0.146 mol) of an aqueous solution of $H_2O_2$ at 30 wt.-%;

100 g of Ludox® AS40 silica ($n_{Si}$=0.6667 mole);

14.75 g of CBMM niobic acid i.e. $n_{Nb}$=0.088 mole; and 33.0 g of Prolabo® oxalic acid i.e. $n_{Oxalate}$=0.262 mol.

259 g of dry precursor are recovered. The precursor is in the form of black sheets on the top and thin yellow-green films underneath.

25 g of this precursor are precalcinated at 321° C. under static air for 4 hours, then calcinated at 598° C. at a flow rate of nitrogen of 51.85 ml/min/g for 2 hours.

A weight of 20.30 g of calcinated solid is obtained. This catalyst is called catalyst B.

Example 10

Preparation of a Catalyst C with the Formula: $Mo_1V_{0.30}Sb_{0.15}Nb_{0.10}Si_{0.93}O_x$ and its Precursor.

Synthesis of the Precursor

A 10 liter reactor with a double jacket is used. The diagram of the installation is given in FIG. 2. The installation comprises the reactor with a double jacket 1, equipped with a draw off 2 and an oil bath 3 thermostatically controlled at 140° C. (so that the temperature inside the reactor is approximately 99° C.), a stirrer 4 designed to operate at 125 r.p.m., an inlet 5 for the reagents, an inlet 6 for the nitrogen, a cooler 7 connected to a vent 8.

2600 g of water, 123 g of ammonium metavanadate (1.052 mole), 77 g of antimony oxide (0.528 mol), and 618 g of ammonium heptamolybdate (3.501 mole) is introduced cold under stirring and under nitrogen flow. After the start of heating, the mixture quickly changes to green, then to blue-black.

After stabilization of the internal temperature of the reactor (T=99° C.), 4 hours of stirring of the solution allow it to be perfectly homogeneous. 60 g of oxygenated water diluted in 500 g of water are added so as to obtain a limpid orange solution (oxidation of all the cations present).

30 minutes later, 491 g (3.27 mole) of colloidal silica is introduced as well as a solution of niobic acid (59 g, 0.5 mol) and oxalic acid (132 g, 1.05 mole) previously heated for two hours and centrifuged (12 minutes at 6200 r.p.m.).

Another 30 minutes later, the heating is stopped but stirring is continued overnight in order to retain a homogeneous solution. The mixture has taken on a yellow colouring and the consistence of a gel.

Forming

A laboratory atomizer (ATSELAB® by Sodeva) is used.

The atomization takes place in an air atmosphere.

The working parameters are globally:
flow rate of nitrogen of the order of 40 m$^3$/h;
flow rate of slurry of the order of 2600 g/h;
inlet temperature of the gas: 290° C.;
outlet temperature of the gas: 134° C.

The increase in the rate of dry material in the slurry is carried out in a rotary evaporator to 30.8 wt.-%.

A fraction comprised between 40 and 160 µm is recovered in the chamber which corresponds to the precursor.

Heat Treatment 26.6 g of the fraction obtained previously, i.e. the precursor, are precalcinated for 4 hours at 316° C. under static air in order to produce a precalcinated solid.

The precalcinated solid is then calcinated for 2 hours at 598° C. under a flow rate of nitrogen of 49.83 ml/g/min and thus produces 21 g of catalyst called CATALYST C.

Example 11

Catalyst Tests a) Apparatus

In order to simulate the process according to the invention, simulations were carried out in the laboratory in a laboratory fixed bed reactor, by generating propane pulses and oxygen pulses.

The following are loaded from the bottom to the top of a vertical reactor with cylindrical shape and made of pyrex:
a first height of 2 ml of silicon carbide in the form of particles of 0.125 mm in diameter,
a second height of 5.00 g of catalyst in the form of particles of 0.02 to 1 mm diluted with 10 ml of silicon carbide in the form of particles of 0.125 mm in diameter,
a third height of 2 ml of silicon carbide in the form of particles of 0.125 mm in diameter, and
a fourth height of silicon carbide in the form of particles of 1.19 mm in diameter, so as to fill all of the reactor.

b) Tests of Catalyst A

1) Operating Process

The reactor is heated to 250° C. and the vaporizer to 200° C. The electric initiation of the water pump is initiated.

Once the reactor and the vaporizer have reached the temperatures given above, the water pump is actuated and the reactor temperature is raised to 400° C. and it is left for 30 minutes so that the hot point is stabilized.

Then, oxygen is introduced in 10 pulses of 23 seconds each in order to sufficiently oxidize the catalyst. The catalyst is considered to be totally oxidized when the temperature of the hot spot has stabilized, i.e. when there is no more exothermal activity due to the reaction (by monitoring the catalyst temperature measured using a thermocouple placed in the catalyst bed, the fluctuations in temperature can be seen as a function of the pulses).

Then the measurements relating to the production of acrylic acid itself can be carried out.

For each balance, liquid samples are taken. Gas samples are also taken using gas bags, each sample representing a certain number of cycles.

Each small gas-washing bottle (with a 25 ml capacity and filled with 20 ml of water) is equipped with a gas bag, and when the bottle is connected to the outlet of the reactor (as soon as the liquid bubbles), the bag is open and the chronometer is started.

In order to verify the oxidation state of the catalyst, another series of ten 23-second pulses of oxygen is carried out. It shows that the oxidation state of the solid has been maintained during the balancing.

The liquid effluents are analyzed on a HP 6890 chromatograph, after having carried out a specific calibration.

The gases are analyzed during the balancing on a Chrompack micro-GC chromatograph.

An assay of the acidity is carried out on each bottle, in order to determine the exact number of moles of acid produced during each microbalancing and to validate the chromatographic analyses.

i) Test TA1

This is a test of the oxidation of propane carried out in the absence of molecular oxygen. This test was carried out with partial pressures of propane and oxygen corresponding to the following ratios:

For the oxidation: propane/He—Kr/H$_2$O: 10/45/45
For the regeneration: O$_2$/He—Kr/H$_2$O: 20/45/45, with a flow rate of He—Kr of 4.262 Nl/h (Nl/h=normal liters per hour), i.e. liters/h at 0° C. and at atmospheric pressure) and at a temperature of 400° C.

In this test, a redox balance is composed of 60 cycles. A redox cycle represents:
12.2 seconds of propane in a continuous flow of helium-krypton/water,
45 seconds of continuous flow of helium-krypton/water,
20 seconds of oxygen in a continuous flow of helium-krypton/water, 45 seconds of continuous flow of helium-krypton/water.

For each balance, 4 liquid samples are carried out, each representing 15 cycles and 4 gas samples using gas bags, each sample representing 15 cycles.

ii) Test TA2

This is also a test of the oxidation of propane carried out in the absence of molecular oxygen.

In this test, the duration of the propane pulse (as well as that of the oxygen) is modified during the balance thus allowing observation of the behaviour of the catalyst when in a more or less rich redox mixture. The duration of the oxygen pulse is still twice as great as that of propane, and with a double flow rate, in order to keep the catalyst oxidized.

The partial pressures of propane and oxygen remain the same as in the preceding test TA1:

For the oxidation: propane/He—Kr/$H_2O$: 10/45/45

For the regeneration: $O_2$/He—Kr/$H_2O$: 20/45/45, with a flow rate of He—Kr of 4.262 Nl/h at a temperature of 400° C.

In this example of 60 cycles the balance is divided into six microbalances in the following way:

2 First Microbalances of 7 and 8 Cycles:
10 seconds of propane in a flow of He—Kr/$H_2O$,
45 seconds under He—Kr,
20 seconds of $O_2$ in a flow of He—Kr,
45 seconds under He—Kr.

$3^{rd}$ Microbalance of 15 Cycles:
5 seconds of propane in a flow of He—Kr/$H_2O$,
50 seconds under He—Kr,
10 seconds of $O_2$ in a flow of He—Kr,
55 seconds under He—Kr.

$4^{th}$ Microbalance of 8 Cycles:
2 seconds of propane in a flow of He—Kr/$H_2O$,
50 seconds under He—Kr,
4 seconds of $O_2$ in a flow of He—Kr,
55 seconds under He—Kr.

$5^{th}$ Microbalance of 8 Cycles:
20 seconds of propane in a flow of He—Kr/$H_2O$,
45 seconds under He—Kr,
40 seconds of $O_2$ in a flow of He—Kr,
45 seconds under He—Kr.

$6^{th}$ Microbalance of 7 Cycles:
30 seconds of propane in a flow of He—Kr/$H_2O$,
45 seconds under He—Kr,
60 seconds of $O_2$ in a flow of He—Kr,
45 seconds under He—Kr.

The durations of the pulses which have just been given are theoretical.

iii) Test TA3

In this test the oxidation of propane is carried out in the presence of molecular oxygen, at 400° C.

The duration of the injection of oxygen in the propane pulse is varied by preserving the constant pressures of propane and of oxygen.

The balance of 40 cycles in this case is broken down as follows:

10 cycles of 30 s of propane+5 s of $O_2$ (the oxygen being injected at the start of the injection of propane), with the proportions propane/$O_2$/He—Kr/$H_2O$ of 30/30/45/45, with a flow of helium-krypton of 4.262 Nl/h.

Then there is an intermediate pulse composed only of the flow of carrier gas He—Kr/$H_2O$ of 60 s, then an oxygen pulse with the proportions $O_2$/He—Kr/$H_2O$ of 20/45/45, for 60 s and another intermediate pulse of He—Kr/$H_2O$ of 60 s.

Then there is another series of 10 cycles of 30 s of propane+10 s of oxygen, with the proportions propane/$O_2$/He—Kr/$H_2O$ of 30/30/45/45, with a flow of helium-krypton of 4.262 Nl/h. Then there is an intermediate pulse composed only of the flow of carrier gas He—Kr/$H_2O$ of 60 s, then an oxygen pulse with the proportions $O_2$/He—Kr/$H_2O$=20/45/45, for 60 s and another intermediate pulse of He—Kr/$H_2O$ of 60 s.

Then, there is another series of 10 cycles of 30 s of propane+15 s of $O_2$, with the proportions propane/$O_2$/He—Kr/$H_2O$ of 30/30/45/45, with a flow of helium-krypton of 4.262 Nl/h. Then there is an intermediate pulse composed only of the flow of carrier gas He—Kr/$H_2O$ of 60 s, then an oxygen pulse with the proportions $O_2$/He—Kr/$H_2O$=20/45/45, for 60 s and another intermediate pulse of He—Kr/$H_2O$ of 60 s.

Then, there is another series of 10 cycles of 30 s of propane+20 s of $O_2$, with the proportions propane/$O_2$/He—Kr/$H_2O$ of 30/30/45/45, with a flow of helium-krypton of 4.262 Nl/h. Then there is an intermediate pulse composed only of the flow of carrier gas He—Kr/$H_2O$ of 60 s, then an oxygen pulse with the proportions $O_2$/He—Kr/$H_2O$ of 20/45/45, for 60 s and another intermediate pulse of He—Kr/$H_2O$ of 60 s.

As in the test TA2, the durations of the pulses which have just been given are theoretical.

2) Results

The results of the tests TA1, TA2 and TA3 are shown in the tables below.

In these tables, the theoretical durations of the pulses are no longer shown as they were previously, but the corresponding real durations which were calculated using a specific calibration.

TABLE 6

| | Test | | |
|---|---|---|---|
| | TA1 | TA2 | TA3 |
| Conditions in the reaction propane/He—Kr/$H_2O$ or propane + $O_2$/He—Kr/$H_2O$ | 10/45/45 | 10/45/45 | 30 + 30/45/45 |
| Conditions in regeneration $O_2$/He—Kr/$H_2O$ | 20/45/45 | 20/45/45 | 20/45/45 |

TABLE 6-continued

|  | Test | | | | | | | | | |
|---|---|---|---|---|---|---|---|---|---|---|
|  | TA1 | TA2 | | | | | TA3 | | | |
| Comments | Standard test | Variation in the duration of the injection of propane during the balance | | | | | Variation in the duration of the injection of $O_2$ in the propane pulse. $O_2$ injection at the start of the propane injection | | | |
| Summary | Average | Flask 4 | Flask 3 | Flask 2 | Flask 5 | Flask 6 | Flask 1 | Flask 2 | Flask 3 | Flask 4 |
| Number of CYCLES | 60 | 15 | 15 | 8 | 8 | 7 | 10 | 10 | 10 | 10 |
| Duration of the propane pulse | 12.2 | 4.4 | 7.6 | 12.9 | 22.5 | 32.8 | 33 | 33.6 | 33.7 | 32.7 |
| Duration of the oxygen pulse injected into the propane | — | — | — | — | — | — | 5 | 10 | 15 | 20 |
| Yields (%) | | | | | | | | | | |
| Acetaldehyde | 0.00 | 0.00 | 0.00 | 0.00 | 0.00 | 0.00 | 0.00 | 0.00 | 0.00 | 0.00 |
| Propylaldehyde | 0.00 | 0.00 | 0.00 | 0.00 | 0.00 | 0.00 | 0.00 | 0.00 | 0.00 | 0.00 |
| Acetone | 0.17 | 0.17 | 0.16 | 0.16 | 0.16 | 0.18 | 0.15 | 0.15 | 0.15 | 0.15 |
| Acrolein | 0.02 | 0.03 | 0.02 | 0.03 | 0.02 | 0.02 | 0.01 | 0.01 | 0.01 | 0.02 |
| Allyl alcohol | 0.02 | 0.03 | 0.02 | 0.00 | 0.00 | 0.00 | 0.00 | 0.00 | 0.00 | 0.00 |
| Allyl acrylate | 0.00 | 0.00 | 0.00 | 0.00 | 0.00 | 0.00 | 0.00 | 0.00 | 0.00 | 0.00 |
| Acetic acid | 1.40 | 1.97 | 1.47 | 1.46 | 1.06 | 1.09 | 0.63 | 0.74 | 0.75 | 0.82 |
| Propionic acid | 0.11 | 0.15 | 0.12 | 0.13 | 0.08 | 0.09 | 0.05 | 0.06 | 0.06 | 0.07 |
| Acrylic acid | 11.43 | 15.80 | 11.79 | 10.25 | 7.88 | 7.50 | 3.68 | 5.21 | 5.77 | 6.59 |
| Carbon monoxide | 1.66 | 2.26 | 1.80 | 1.68 | 1.24 | 1.07 | 0.64 | 0.70 | 0.80 | 0.90 |
| Carbon dioxide | 0.81 | 1.23 | 0.87 | 0.91 | 0.75 | 0.60 | 0.83 | 0.44 | 0.50 | 0.56 |
| Propylene | 3.56 | 3.56 | 3.70 | 3.65 | 3.57 | 3.44 | 3.34 | 3.57 | 3.76 | 3.87 |
| Propane | 79.60 | 75.02 | 80.04 | 82.11 | 85.21 | 85.74 | 90.58 | 89.26 | 87.76 | 87.01 |
| Carbon balance (%) | 98.8 | 100.2 | 100.0 | 100.4 | 100.0 | 99.7 | 99.9 | 100.1 | 99.6 | 100.0 |

TABLE 7

|  | Test | | | | | | | | | |
|---|---|---|---|---|---|---|---|---|---|---|
|  | TA1 | TA2 | | | | | TA3 | | | |
| Conditions in the reaction propane/He—Kr/$H_2O$ or propane + $O_2$/He—Kr/$H_2O$ | 10/45/45 | 10/45/45 | | | | | 30 + 30/45/45 | | | |
| Conditions in regeneration $O_2$/He—Kr/$H_2O$ | 20/45/45 | 20/45/45 | | | | | 20/45/45 | | | |
| Comments | Standard test | Variation in the duration of the propane pulse during the balance | | | | | Variation in the duration of the injection of $O_2$ in the propane pulse | | | |
| Summary | Average | Flask 4 | Flask 3 | Flask 2 | Flask 5 | Flask 6 | Flask 1 | Flask 2 | Flask 3 | Flask 4 |
| Number of CYCLES | 60 | 15 | 15 | 8 | 8 | 7 | 10 | 10 | 10 | 10 |
| Duration of the propane injection | 12.2 | 4.4 | 7.6 | 12.9 | 22.5 | 32.8 | 33 | 33.6 | 33.7 | 32.7 |
| Duration of the oxygen pulses injected into the propane | | | | | | | 5 | 10 | 15 | 20 |
| Selectivities (%) | | | | | | | | | | |
| Acetaldehyde | 0.00 | 0.00 | 0.00 | 0.00 | 0.00 | 0.00 | 0.04 | 0.03 | 0.00 | 0.03 |
| Propanaldehyde | 0.00 | 0.00 | 0.00 | 0.00 | 0.00 | 0.00 | 0.00 | 0.00 | 0.00 | 0.00 |
| Acetone | 0.91 | 0.66 | 0.78 | 0.89 | 1.05 | 1.28 | 1.58 | 1.39 | 1.26 | 1.14 |
| Acrolein | 0.12 | 0.13 | 0.12 | 0.15 | 0.13 | 0.14 | 0.14 | 0.12 | 0.12 | 0.12 |
| Allyl alcohol | 0.10 | 0.13 | 0.08 | 0.00 | 0.00 | 0.00 | 0.04 | 0.03 | 0.03 | 0.03 |
| Allyl acrylate | 0.00 | 0.00 | 0.00 | 0.00 | 0.00 | 0.00 | 0.00 | 0.00 | 0.00 | 0.00 |
| Acetic acid | 7.31 | 7.81 | 7.38 | 8.00 | 7.17 | 7.82 | 6.71 | 6.77 | 6.33 | 6.30 |
| Propionic acid | 0.56 | 0.58 | 0.58 | 0.70 | 0.53 | 0.64 | 0.58 | 0.56 | 0.53 | 0.51 |
| Acrylic acid | 59.56 | 62.69 | 59.14 | 56.10 | 53.45 | 53.60 | 39.37 | 47.83 | 48.88 | 50.82 |
| Carbon monoxide | 8.64 | 8.98 | 9.01 | 9.22 | 8.41 | 7.64 | 6.88 | 6.39 | 6.78 | 6.93 |
| Carbon dioxide | 4.22 | 4.88 | 4.35 | 4.97 | 5.07 | 4.32 | 8.88 | 4.04 | 4.24 | 4.33 |
| Propylene | 18.56 | 14.13 | 18.56 | 19.96 | 24.19 | 24.57 | 35.78 | 32.83 | 31.83 | 29.80 |
| Quantity of $O_2$ consumed (g O/kg catalyst) | 0.32 | 0.158 | 0.207 | 0.321 | 0.436 | 0.589 | 1.16 | 1.30 | 1.43 | 1.56 |
| μmole of propane for 1 cycle | 131.8 | 47.5 | 82.1 | 139.4 | 243.1 | 354.4 | 1072 | 1091 | 1094 | 1062 |
| μmole $O_2$ added per cycle | — | — | — | — | — | — | 158 | 317 | 475 | 634 |
| μmole of $O_2$ consumed (products formed)/cycle | — | — | — | — | — | — | 363 | 405 | 448 | 488 |
| Propane conversion ratio (kg/catalyst/kg converted propane) | 4233 | 9584 | 6942 | 4565 | 3166 | 2253 | 1107 | 971 | 852 | 803 |

In test TA3, where the operation takes place in the presence of molecular oxygen, it is noted that the yields of acid acrylic increase much more quickly, as a function of the addition of oxygen in the propane pulse, than the yields in $CO_x$ and acetic acid. A substantial gain in acrylic acid selectivity results. A lowering of the selectivity of hydration products is also observed (acetone, propionic acid).

The addition of oxygen also leads to a gain in conversion ratio which thus changes from 1107 to 803 kg/kg.

c) Tests of Catalyst B

1) Operating Process

The apparatus used is the one described in Example 11 a).

i) Tests TB 1 and TB2

Catalyst B is tested under the same conditions and in the same way as for test TA1.

ii) Test TB3

Catalyst B is tested under the same conditions and in the same way as for test TA3 (presence of molecular oxygen).

iii) Tests TB4 to TB6

In the case of test TB4, catalyst B is tested under the same conditions and in the same way as for test TA2, at 420° C.

In the case of tests TB5 and TB6, there is simply modification of the content of propane during the oxidation and of oxygen during the regeneration.

iv) Tests TB7

In this test, the oxidation of propane is carried out in the presence of molecular oxygen, at 420° C.

The duration of the injection of oxygen in the propane pulse is varied by keeping the pressures of propane and of oxygen constant.

The oxygen is injected at the end of the propane pulse to see if there is an influence on the catalytic performances compared to an injection at the start of the pulse.

The balance of 40 cycles is broken down as follows:

10 cycles of 30 s of propane+20 s of $O_2$ (the oxygen being injected at the end of the propane pulse), with the proportions propane/$O_2$/He—Kr/$H_2O$ of 30/30/45/45, with a flow of helium-krypton of 4.27 Nl/h.

Then there is an intermediate pulse composed only of the flow of carrier gas He—Kr/$H_2O$ of 60 s, then a pulse of $O_2$ with the proportions $O_2$/He—Kr/$H_2O$=20/45/45, for 60 s and another pulse of carrier gas of 60 s.

Then, there is another series of 10 cycles of 30 s of propane+15 s of oxygen, with the proportions propane/$O_2$/He—Kr/$H_2O$ of 30/30/45/45, with a flow of helium-krypton of 4.27 Nl/h. Then there is an intermediate pulse composed only of the flow of carrier gas He—Kr/H2O of 60 s, then an oxygen pulse with the proportions $O_2$/He—Kr/$H_2O$=20/45/45, for 60 s and another intermediate pulse of carrier gas of 60 s. Then, there is another series of 10 cycles of 30 s of propane+10 s of $O_2$, with the proportions propane/$O_2$/He—Kr/$H_2O$ of 30/30/45/45, with a flow of helium-krypton of 4.27 Nl/h. Then there is an intermediate pulse composed only of the flow of carrier gas He—Kr/$H_2O$ of 60 s, then a pulse of $O_2$ with the proportions $O_2$/He—Kr/$H_2O$=20/45/45, for 60 s and another intermediate pulse of carrier gas of 60 s.

Then, there is another series of 10 cycles of 30 s of propane+5 s of $O_2$, with the proportions propane/$O_2$/He—Kr/$H_2O$ of 30/30/45/45, with a flow of helium-krypton of 4.27 Nl/h. Then there is an intermediate pulse composed only of the flow of carrier gas He—Kr/$H_2O$ of 60 s, then a pulse of $O_2$ with the proportions $O_2$/He—Kr/$H_2O$=20/45/45, for 60 s and another intermediate pulse of carrier gas of 60 s.

v) Tests TB8

In this test, there is also oxidation of the propane in the presence of molecular oxygen.

There is comparison of the effect of the injection of oxygen at the end and at the start of the propane pulse by keeping constant pressures of propane and of oxygen but also a constant duration of injection of oxygen in the propane pulse.

The balance of 40 cycles is broken down as follows:

10 cycles of 30 s of propane+20 s of $O_2$ (the oxygen being injected at the end of the propane pulse), with the proportions propane/$O_2$/He—Kr/$H_2O$ of 30/30/45/45, with a flow of helium-krypton of 4.27 Nl/h. Then there is an intermediate pulse composed only of the flow of carrier gas He—Kr/$H_2O$ of 60 s, then an intermediate pulse of $O_2$ with the proportions $O_2$/He—Kr/$H_2O$=20/45/45, for 60 s and another intermediate pulse of carrier gas of 60 s.

Then, there is another series of 10 cycles of 30 s of propane+20 s of oxygen ($O_2$ being injected at the end of the propane pulse), with the proportions propane/$O_2$/He—Kr/$H_2O$ of 30/30/45/45, with a flow of helium-krypton of 4.27 Nl/h. Then there is an intermediate pulse composed only of the flow of carrier gas He—Kr/$H_2O$ of 60 s, then an intermediate pulse of oxygen with the proportions $O_2$/He—Kr/$H_2O$=20/45/45, for 60 s and another intermediate pulse of carrier gas of 60 s.

10 cycles of 30 s of propane+20 s of $O_2$ (the oxygen being injected at the start of the propane pulse), with the proportions propane/$O_2$/He—Kr/$H_2O$ of 30/30/45/45, with a flow of helium-krypton of 4.27 Nl/h. Then, there is an intermediate pulse composed only of the flow of carrier gas He—Kr/$H_2O$ of 60 s, then, an intermediate pulse of $O_2$ with the proportions $O_2$/He—Kr/$H_2O$=20/45/45, for 60 s and another intermediate pulse of carrier gas of 60 s.

Then, there is another series of 10 cycles of 30 s of propane+20 s of $O_2$ (the oxygen being injected at the start of the propane pulse), with the proportions propane/$O_2$/He—Kr/$H_2O$ of 30/30/45/45, with a flow of helium-krypton of 4.27 Nl/h. Then, there is an intermediate pulse composed only of the flow of carrier gas He—Kr/$H_2O$ of 60 s, then an intermediate pulse of $O_2$ with the proportions $O_2$/He—Kr/$H_2O$=20/45/45, for 60 s and another intermediate pulse of carrier gas of 60 s.

2) Results of the Tests a) Tests TB1 and TB2

TABLE 8

|  | Test | |
| --- | --- | --- |
|  | TB1 | TB2 |
| Conditions in the reaction propane/He—Kr/$H_2O$ | 10/45/45 | 10/45/45 |
| Conditions in regeneration O2/He—Kr/$H_2O$ | 20/45/45 | 20/45/45 |
| Temperature (° C.) | 400 | 420 |
| Summary | Average | Average |
| Number of CYCLES | 60 | 60 |
| Duration of the injection of propane | 12.06 | 12.06 |
| Yields (%) | | |
| Acetaldehyde | 0.00 | 0.00 |
| Propanaldehyde | 0.00 | 0.00 |
| Acetone | 0.22 | 0.17 |

TABLE 8-continued

| | Test | |
|---|---|---|
| | TB1 | TB2 |
| Acrolein | 0.00 | 0.01 |
| Allyl alcohol | 0.00 | 0.00 |
| Allyl acrylate | 0.00 | 0.00 |
| Acetic acid | 2.04 | 2.72 |
| Propionic acid | 0.08 | 0.04 |
| Acrylic acid | 13.0 | 15.3 |
| Carbon monoxide | 2.48 | 4.47 |
| Conditions in the reaction propane/He—Kr/$H_2O$ | 10/45/45 | 10/45/45 |
| Conditions in regeneration O2/He—Kr/$H_2O$ | 20/45/45 | 20/45/45 |
| Temperature (° C.) | 400 | 420 |
| Summary | Average | Average |
| Number of CYCLES | 60 | 60 |
| Duration of the injection of propane | 12.06 | 12.06 |
| Carbon dioxide | 1.44 | 2.92 |
| Propylene | 3.42 | 3.69 |
| Propane | 74.7 | 71.2 |
| Carbon balance (%) | 97.4 | 100.5 |
| Selectivities (%) | | |
| Acetaldehyde | 0.00 | 0.00 |
| Propanaldehyde | 0.00 | 0.00 |
| Acetone | 0.99 | 0.59 |
| Acrolein | 0.00 | 0.03 |
| Allyl alcohol | 0.00 | 0.00 |
| Allyl acrylate | 0.00 | 0.00 |
| Acetic acid | 8.99 | 9.25 |
| Propionic acid | 0.33 | 0.15 |
| Acrylic acid | 57.4 | 52.2 |
| Carbon monoxide | 10.9 | 15.2 |
| Carbon dioxide | 6.3 | 10.0 |
| Propylene | 15.1 | 12.6 |
| Quantity of $O_2$ consumed (g O/kg catalyst) | 0.42 | 0.59 |

TABLE 8-continued

| | Test | |
|---|---|---|
| | TB1 | TB2 |
| μmole of propane for 1 cycle | 135.9 | 135.9 |
| Propane conversion ratio | 3309 | 2904 |
| (kg catalyst/kg converted propane) | | |

A better conversion is observed at 420° C. than at 400° C. The acrylic acid selectivity changes from 57.4% to 52.2% when the temperature is modified. A clear decrease (division by two) of the selectivities of acetone and propionic acid is observed.

The fact of increasing the temperature allows the conversion to be increased and the formation of hydration products as well as the conversion ratio to be decreased.

The conversion ratio changes from 3300 to 2900 kg/kg by changing from 400 to 420° C.

b) Tests TB4 to TB6

The results appear in the two tables below.

It is observed that the increase in the partial pressure of propane and/or of the duration of the injection of propane leads to a decrease in the yield of acrylic acid, but to the same yield of hydration products. The selectivities of hydration products therefore increase with the reduction of the catalyst. The selectivities of acrolein and propylene also increase with the reduction of the catalyst. The reduced catalyst becomes less active.

TABLE 9

| | Test | | | | | | | |
|---|---|---|---|---|---|---|---|---|
| | TB4 | | | | | TB5 | | |
| Conditions in the reaction propane/He—Kr/$H_2O$ | 10/45/45 | | | | | 20/45/45 | | |
| Conditions in regeneration O2/He—Kr/$H_2O$ | 20/45/45 | | | | | 20/45/45 | | |
| Summary | Flask 4 | Flask 3 | Flask 2 | Flask 5 | Flask 6 | Flask 4 | Flask 3 | Flask 2 |
| Number of CYCLES | 15 | 15 | 8 | 8 | 7 | 15 | 15 | 8 |
| Duration of the injection of propane | 4.5 | 7.4 | 12.35 | 21.4 | 30.6 | 4.4 | 7.5 | 12.6 |
| Yields (%) | | | | | | | | |
| Acetaldehyde | 0.00 | 0.00 | 0.00 | 0.00 | 0.00 | 0.00 | 0.00 | 0.00 |
| Propanaldehyde | 0.00 | 0.00 | 0.00 | 0.00 | 0.00 | 0.00 | 0.00 | 0.00 |
| Acetone | 0.15 | 0.16 | 0.20 | 0.22 | 0.24 | 0.20 | 0.21 | 0.23 |
| Acrolein | 0.00 | 0.00 | 0.00 | 0.00 | 0.02 | 0.00 | 0.02 | 0.02 |
| Allyl alcohol | 0.00 | 0.00 | 0.00 | 0.00 | 0.00 | 0.00 | 0.00 | 0.00 |
| Allyl acrylate | 0.00 | 0.00 | 0.00 | 0.00 | 0.00 | 0.00 | 0.00 | 0.00 |
| Acetic acid | 3.56 | 2.67 | 2.71 | 2.53 | 2.28 | 2.84 | 2.62 | 2.30 |
| Propionic acid | 0.05 | 0.05 | 0.05 | 0.04 | 0.04 | 0.05 | 0.05 | 0.04 |
| Acrylic acid | 24.00 | 19.06 | 15.96 | 11.84 | 9.81 | 15.61 | 13.39 | 10.03 |
| Carbon monoxide | 5.75 | 4.73 | 3.97 | 3.20 | 2.74 | 3.86 | 3.28 | 2.56 |
| Carbon dioxide | 3.40 | 2.48 | 2.51 | 2.15 | 2.00 | 2.38 | 2.16 | 2.05 |
| Propylene | 3.26 | 3.57 | 3.62 | 3.71 | 3.67 | 3.82 | 3.76 | 3.81 |
| Propane | 60.36 | 67.20 | 70.96 | 76.34 | 79.25 | 71.46 | 74.03 | 79.25 |
| Carbon balance (%) | 100.5 | 99.9 | 100.0 | 100.0 | 100.0 | 100.2 | 99.5 | 100.3 |

| | Test | |
|---|---|---|
| | TB5 | TB6 |
| Conditions in the reaction propane/He—Kr/$H_2O$ | 20/45/45 | 30/45/45 |
| Conditions in regeneration O2/He—Kr/$H_2O$ | 20/45/45 | 30/45/45 |

TABLE 9-continued

| Summary | Flask 5 | Flask 6 | Flask 4 | Flask 3 | Flask 2 | Flask 5 | Flask 6 |
|---|---|---|---|---|---|---|---|
| Number of CYCLES | 8 | 6? | 15 | 15 | 8 | 8 | 7 |
| Duration of the injection of propane | 22.7 | 31.8 | 4.35 | 6.85 | 12.3 | 21.8 | 29.9 |
| Yields (%) | | | | | | | |
| Acetaldehyde | 0.00 | 0.00 | 0.00 | 0.00 | 0.00 | 0.01 | 0.01 |
| Propanaldehyde | 0.00 | 0.00 | 0.00 | 0.00 | 0.00 | 0.00 | 0.00 |
| Acetone | 0.25 | 0.25 | 0.21 | 0.20 | 0.24 | 0.24 | 0.23 |
| Acrolein | 0.02 | 0.02 | 0.02 | 0.02 | 0.03 | 0.02 | 0.02 |
| Allyl alcohol | 0.00 | 0.00 | 0.00 | 0.00 | 0.00 | 0.00 | 0.00 |
| Allyl acrylate | 0.00 | 0.00 | 0.00 | 0.00 | 0.00 | 0.00 | 0.00 |
| Acetic acid | 1.74 | 1.56 | 2.67 | 2.00 | 1.89 | 1.37 | 1.21 |
| Propionic acid | 0.04 | 0.04 | 0.05 | 0.04 | 0.04 | 0.04 | 0.03 |
| Acrylic acid | 6.84 | 5.80 | 13.60 | 8.88 | 8.00 | 5.28 | 4.44 |
| Carbon monoxide | 1.67 | 1.46 | 3.32 | 2.58 | 1.88 | 1.21 | 1.07 |
| Carbon dioxide | 1.40 | 1.29 | 2.34 | 2.07 | 1.59 | 1.10 | 0.96 |
| Propylene | 3.77 | 3.55 | 3.88 | 3.85 | 3.84 | 3.65 | 3.42 |
| Propane | 84.20 | 85.95 | 74.10 | 80.27 | 82.75 | 87.11 | 88.50 |
| Carbon balance (%) | 99.9 | 99.9 | 100.2 | 99.9 | 100.3 | 100.0 | 99.9 |

TABLE 10

| | Test | | | | | | | |
|---|---|---|---|---|---|---|---|---|
| | TB4 | | | | | TB5 | | |
| Conditions in the reaction Propane/He—Kr/H$_2$O | 10/45/45 | | | | | 20/45/45 | | |
| Conditions in regeneration O$_2$/He—Kr/H$_2$O | 20/45/45 | | | | | 20/45/45 | | |
| Summary | Flask 4 | Flask 3 | Flask 2 | Flask 5 | Flask 6 | Flask 4 | Flask 3 | Flask 2 |
| Number of cycles | 15 | 15 | 8 | 8 | 7 | 15 | 15 | 8 |
| Duration of the injection of propane | 4.5 | 7.4 | 12.35 | 21.4 | 30.6 | 4.4 | 7.5 | 12.6 |
| Yields (%) | | | | | | | | |
| Acetaldehyde | 0.00 | 0.00 | 0.00 | 0.00 | 0.00 | 0.00 | 0.00 | 0.00 |
| Propanaldehyde | 0.00 | 0.00 | 0.00 | 0.00 | 0.00 | 0.00 | 0.00 | 0.00 |
| Acetone | 0.37 | 0.48 | 0.68 | 0.94 | 1.13 | 0.70 | 0.83 | 1.11 |
| Acrolein | 0.00 | 0.00 | 0.00 | 0.00 | 0.11 | 0.00 | 0.08 | 0.12 |
| Allyl alcohol | 0.00 | 0.00 | 0.00 | 0.00 | 0.00 | 0.00 | 0.00 | 0.00 |
| Allyl acrylate | 0.00 | 0.00 | 0.00 | 0.00 | 0.00 | 0.00 | 0.00 | 0.00 |
| Acetic acid | 8.86 | 8.17 | 9.34 | 10.66 | 10.97 | 9.89 | 10.27 | 10.91 |
| Propionic acid | 0.11 | 0.15 | 0.18 | 0.19 | 0.21 | 0.19 | 0.20 | 0.21 |
| Acrylic acid | 59.77 | 58.26 | 54.99 | 49.96 | 47.15 | 54.27 | 52.54 | 47.64 |
| Carbon monoxide | 14.31 | 14.45 | 13.69 | 13.52 | 13.16 | 13.41 | 12.86 | 12.17 |
| Carbon dioxide | 8.47 | 7.58 | 8.66 | 9.08 | 9.60 | 8.26 | 8.46 | 9.74 |
| Propylene | 8.11 | 10.91 | 12.47 | 15.66 | 17.67 | 13.29 | 14.76 | 18.11 |
| Quantity of oxygen consumed (g O/kg catalysts) | 0.305 | 0.397 | 0.586 | 0.815 | 1.012 | 0.387 | 0.578 | 0.793 |
| µmole of propane/1 cycle | 50.7 | 83.4 | 139.2 | 241.2 | 344.9 | 94.0 | 160.2 | 269.1 |
| Propane conversion ratio (kg catalyst/kg converted propane) | 5659 | 4159 | 2815 | 1994 | 1590 | 4243 | 2736 | 2038 |

| | Test | | | | | | |
|---|---|---|---|---|---|---|---|
| | TB5 | | | | TB6 | | |
| Conditions in the reaction Propane/He—Kr/H$_2$O | 20/45/45 | | | | 30/45/45 | | |
| Conditions in regeneration O$_2$/He—Kr/H$_2$O | 20/45/45 | | | | 30/45/45 | | |
| Summary | Flask 5 | Flask 6 | Flask 4 | Flask 3 | Flask 2 | Flask 5 | Flask 6 |
| Number of cycles | 8 | 6 | 15 | 15 | 8 | 8 | 7 |
| Duration of the injection of propane | 22.7 | 31.8 | 4.35 | 6.85 | 12.3 | 21.8 | 29.9 |
| Yields (%) | | | | | | | |
| Acetaldehyde | 0.00 | 0.00 | 0.00 | 0.00 | 0.00 | 0.05 | 0.06 |
| Propanaldehyde | 0.00 | 0.00 | 0.00 | 0.00 | 0.00 | 0.00 | 0.00 |
| Acetone | 1.58 | 1.80 | 0.79 | 1.02 | 1.37 | 1.87 | 2.00 |
| Acrolein | 0.14 | 0.16 | 0.08 | 0.10 | 0.14 | 0.18 | 0.17 |
| Allyl alcohol | 0.00 | 0.00 | 0.00 | 0.00 | 0.00 | 0.00 | 0.00 |
| Allyl acrylate | 0.00 | 0.00 | 0.00 | 0.00 | 0.00 | 0.00 | 0.00 |

TABLE 10-continued

| | | | | | | | |
|---|---|---|---|---|---|---|---|
| Acetic acid | 11.04 | 11.19 | 10.22 | 10.18 | 10.81 | 10.59 | 10.66 |
| Propionic acid | 0.26 | 0.26 | 0.20 | 0.21 | 0.24 | 0.29 | 0.28 |
| Acrylic acid | 43.51 | 41.51 | 52.14 | 45.22 | 45.69 | 40.89 | 38.98 |
| Carbon monoxide | 10.62 | 10.48 | 12.72 | 13.12 | 10.72 | 9.36 | 9.40 |
| Carbon dioxide | 8.88 | 9.20 | 8.97 | 10.55 | 9.09 | 8.53 | 8.46 |
| Propylene | 23.97 | 25.39 | 14.87 | 19.60 | 21.94 | 28.24 | 29.99 |
| Quantity of oxygen consumed (g O/kg catalysts) | 0.998 | 1.232 | 0.525 | 0.617 | 0.934 | 1.141 | 1.360 |
| μmole of propane/1 cycle | 484.7 | 679.1 | 141.3 | 222.5 | 399.5 | 708.0 | 971.1 |
| Propane conversion ratio (kg catalyst/kg converted propane) | 1486 | 1193 | 3110 | 2593 | 1652 | 1247 | 1019 | c) Tests TB3, TB7 and TB8

The results appear in the three tables below.

It is observed that the addition of molecular oxygen allows a clear decrease in the conversion ratio while maintaining a good selectivity. There is a change from 2904 kg of catalyst/kg of converted propane for a standard test to 1019 kg of catalyst/kg of converted propane for a test with variation of pulse duration (30 s of propane with propane or oxygen/He—Kr/H$_2$O: 30 or 30/45/45). With the addition of oxygen it is from 460 to 500 kg of catalyst/kg of converted propane.

It is advantageous to add oxygen which allows not only a further decrease of the conversion ratio, but also an increase in the acrylic acid selectivities. It is observed that the catalyst, even reduced, can remain dehydrogenating.

TABLE 11

| | Test | | | | | | | | | | | |
|---|---|---|---|---|---|---|---|---|---|---|---|---|
| | TB3 | | | | TB7 | | | | TB8 | | | |
| Conditions in the reaction propane + O$_2$/He—Kr/H$_2$O | 30 + 30/45/45 | | | | 30 + 30/45/45 | | | | 30 + 30/45/45 | | | |
| Conditions in regeneration O$_2$/He—Kr/H$_2$O | 20/45/45 | | | | 20/45/45 | | | | 20/45/45 | | | |
| Comments | Variation in the duration of the injection of O$_2$ in the propane pulse | | | | Variation in the duration of the injection of O$_2$ in the propane pulse. Injection of O$_2$ at the end of the pulse | | | | Duration of O$_2$ injection into the constant propane pulse. Injection of O$_2$ at the end of the pulse then at the start of the pulse | | | |
| Summary | Flask 1 | Flask 2 | Flask 3 | Flask 4 | Flask 1 | Flask 2 | Flask 3 | Flask 4 | Flask 1 | Flask 2 | Flask 3 | Flask 4 |
| Number of CYCLES | 10 | 10 | 10 | 10 | 10 | 10 | 10 | 10 | 10 | 10 | 10 | 10 |
| Duration of the injection of propane | 33.3 | 34.4 | 34.2 | 34.6 | 34.4 | 36.5 | 34.2 | 33.6 | 34.4 | 34.3 | 34.6 | 35 |
| Duration of the oxygen pulse injected into the propane pulse | 5 | 10 | 15 | 20 | 20 | 15 | 10 | 5 | 20 | 20 | 20 | 20 |
| Yields (%) | | | | | | | | | | | | |
| Acetaldehyde | 0.01 | 0.01 | 0.01 | 0.00 | 0.01 | 1 | 0.01 | 0.01 | 0.00 | 0.00 | 0.00 | 0.00 |
| Propanaldehyde | 0.00 | 0.00 | 0.00 | 0.00 | 0.00 | | 0.00 | 0.00 | 0.00 | 0.00 | 0.00 | 0.00 |
| Acetone | 0.20 | 0.20 | 0.19 | 0.16 | 0.06 | | 0.08 | 0.05 | 0.15 | 0.15 | 0.17 | 0.17 |
| Acrolein | 0.02 | 0.02 | 0.02 | 0.02 | 0.02 | | 0.02 | 0.01 | 0.02 | 0.02 | 0.02 | 0.02 |
| Allyl alcohol | 0.00 | 0.00 | 0.00 | 0.00 | 0.00 | | 0.00 | 0.00 | 0.00 | 0.00 | 0.00 | 0.00 |
| Allyl acrylate | 0.00 | 0.00 | 0.00 | 0.00 | 0.00 | | 0.00 | 0.00 | 0.00 | 0.00 | 0.00 | 0.00 |
| Acetic acid | 1.48 | 1.55 | 1.68 | 1.76 | 1.76 | | 1.51 | 1.42 | 1.77 | 1.69 | 1.89 | 1.87 |
| Propionic acid | 0.03 | 0.04 | 0.04 | 0.04 | 0.04 | | 0.04 | 0.03 | 0.04 | 0.04 | 0.04 | 0.04 |
| Acrylic acid | 6.86 | 8.30 | 9.86 | 11.04 | 10.33 | | 6.98 | 5.57 | 10.64 | 10.21 | 11.54 | 11.40 |
| Carbon monoxide | 1.61 | 1.73 | 2.02 | 2.34 | 2.42 | | 1.79 | 1.50 | 2.69 | 2.54 | 2.53 | 2.47 |
| Carbon dioxide | 1.37 | 1.41 | 1.52 | 1.77 | 1.95 | | 1.59 | 1.36 | 2.08 | 1.98 | 2.02 | 2.00 |
| Propylene | 3.70 | 3.99 | 4.17 | 4.27 | 4.09 | | 3.70 | 3.49 | 4.06 | 4.08 | 4.20 | 4.22 |
| Propane | 84.96 | 82.92 | 80.65 | 78.78 | 79.61 | | 84.51 | 86.81 | 78.74 | 79.38 | 77.79 | 77.78 |
| Carbon balance (%) | 100.2 | 100.2 | 100.1 | 100.2 | 100.3 | | 100.2 | 100.2 | 100.2 | 100.1 | 100.2 | 100.0 |
| Conditions in the reaction propane + O$_2$/He—Kr/H$_2$O | 30 + 30/45/45 | | | | 30 + 30/45/45 | | | | 30 + 30/45/45 | | | |
| Conditions in regeneration O$_2$/He—Kr/H$_2$O | 20/45/45 | | | | 20/45/45 | | | | 20/45/45 | | | |
| Comments | Variation in the duration of the injection of O$_2$ in the propane pulse | | | | Variation in the duration of the injection of O$_2$ in the propane pulse. Injection of O$_2$ at the end of the pulse | | | | Duration of O$_2$ injection into the constant propane pulse. Injection of O$_2$ at the end of the pulse then at the start of the pulse | | | |
| Summary | Flask 1 | Flask 2 | Flask 3 | Flask 4 | Flask 1 | Flask 2 | Flask 3 | Flask 4 | Flask 1 | Flask 2 | Flask 3 | Flask 4 |
| Number of CYCLES | 10 | 10 | 10 | 10 | 10 | 10 | 10 | 10 | 10 | 10 | 10 | 10 |

TABLE 11-continued

| | Test | | | | | | | | | | | |
|---|---|---|---|---|---|---|---|---|---|---|---|---|
| | TB3 | | | | | TB7 | | | | TB8 | | |
| Duration of the injection of propane | 33.3 | 34.4 | 34.2 | 34.6 | 34.4 | 36.5 | 34.2 | 33.6 | 34.4 | 34.3 | 34.6 | 35 |
| Duration of the $O_2$ pulses injected into the propane pulse | 5 | 10 | 15 | 20 | 20 | 15 | 10 | 5 | 20 | 20 | 20 | 20 |
| Selectivities (%) | | | | | | | | | | | | |
| Acetaldehyde | 0.05 | 0.03 | 0.03 | 0.02 | 0.02 | [1] | 0.04 | 0.05 | 0.02 | 0.02 | 0.02 | 0.02 |
| Propanaldehyde | 0.00 | 0.00 | 0.00 | 0.00 | 0.00 | | 0.00 | 0.00 | 0.00 | 0.00 | 0.00 | 0.0 |
| Acetone | 1.33 | 1.15 | 0.96 | 0.77 | 0.31 | | 0.49 | 0.38 | 0.71 | 0.74 | 0.77 | 0.78 |
| Acrolein | 0.12 | 0.13 | 0.11 | 0.10 | 0.09 | | 0.11 | 0.11 | 0.07 | 0.07 | 0.07 | 0.07 |
| Allyl alcohol | 0.00 | 0.00 | 0.00 | 0.00 | 0.00 | | 0.00 | 0.0 | 0.00 | 0.00 | 0.00 | 0.00 |
| Allyl acrylate | 0.00 | 0.00 | 0.00 | 0.00 | 0.00 | | 0.00 | 0.0 | 0.00 | 0.00 | 0.00 | 0.00 |
| Acetic acid | 9.69 | 8.98 | 8.60 | 8.21 | 8.52 | | 9.59 | 10.56 | 8.24 | 8.18 | 8.42 | 8.44 |
| Propionic acid | 0.21 | 0.22 | 0.21 | 0.19 | 0.20 | | 0.23 | 0.25 | 0.19 | 0.21 | 0.19 | 0.19 |
| Acrylic acid | 44.85 | 48.11 | 50.59 | 51.56 | 49.94 | | 44.48 | 41.42 | 49.59 | 49.28 | 51.48 | 51.34 |
| Carbon monoxide | 10.56 | 10.06 | 10.34 | 10.95 | 11.69 | | 11.41 | 11.15 | 12.52 | 12.27 | 11.30 | 11.11 |
| Carbon dioxide | 8.99 | 8.20 | 7.80 | 8.27 | 9.42 | | 10.11 | 10.15 | 9.72 | 9.54 | 8.99 | 9.03 |
| Propylene | 24.21 | 23.12 | 21.37 | 19.93 | 19.80 | | 23.53 | 25.94 | 18.94 | 19.68 | 18.75 | 19.02 |

[1]An analysis problem was detected on flask 2, for this reason the results obtained are not shown.

d) Tests of Catalyst C

1) Operating Process

The apparatus used is that described in Example 11 a).

i) Test TC1

Catalyst C is tested in the same way as for test TA1. The conditions are the same with the exception of the flow rate of He—Kr which is 4.27 Nl/h and the temperature of the test which is 420° C.

ii) Tests TC2 to TC4

In the case of test TC2, the catalyst C is tested under the same conditions and in the same way as for test TA2. In the case of tests TC3 and TC4, there is simply modification of the content of propane during the oxidation and of oxygen during the regeneration.

These three tests were carried out at 420° C. and with a flow rate of He—Kr of 4.27 Nl/h.

iii) Test TC5

Catalyst C is tested in the same way as for test TA3 (presence of molecular oxygen). The conditions are also identical except for the flow rate of He—Kr which is now 4.27 Nl/h. The temperature is 420° C.

iv) Test TC6

Catalyst C is tested in the same way as for test TB7. The conditions are identical.

v) Test TC7

Catalyst C is tested in the same way as for test TB8. The conditions are identical except for the flow rate of He—Kr which is 4.27 Nl/h and the temperature of the test which is 420° C.

2) Results a) Tests TC1 to TC4

The results are shown in the two tables below.

It is observed, as for catalyst B, that the selectivity of propionic acid and acetone increases with the partial pressure of propane, i.e. the more the catalyst is reduced the less selective it is.

The kinetics of initial oxygen consumption is very fast, then appears to develop as a function of the time.

TABLE 12

| | Test | | | | | | | | | |
|---|---|---|---|---|---|---|---|---|---|---|
| | TC1 | | TC2 | | | | TC3 | | | |
| Conditions in the reaction propane + $O_2$/He—Kr/$H_2O$ | 10/45/45 | | 10/45/45 | | | | 20/45/45 | | | |
| Conditions in regeneration $O_2$/He—Kr/$H_2O$ | 20/45/45 | | 20/45/45 | | | | 20/45/45 | | | |
| Comments | Standard test | | Variation of the duration of the propane pulse in the mixture | | | | Variation of the duration of the propane pulse in the mixture | | | |
| Summary | Average | Flask 4 | Flask 3 | Flask 2 | | Flask 6 | Flask 4 | Flask 3 | Flask 2 |
| Number of CYCLES | 60 | 15 | 15 | 8 | 8 | 7 | 15 | 15 | 8 |
| Duration of the injection of propane | 12.2 | 4.45 | 7.7 | 12.5 | 22.2 | 31.8 | 4.45 | 7.6 | 12.65 |
| Yields (%) | | | | | | | | | |
| Acetaldehyde | 0.03 | 0.00 | 0.00 | 0.00 | 0.00 | 0.01 | 0.00 | 0.01 | 0.01 |

TABLE 12-continued

| | | | | | | | | | |
|---|---|---|---|---|---|---|---|---|---|
| Propanaldehyde | 0.00 | 0.00 | 0.00 | 0.00 | 0.00 | 0.00 | 0.00 | 0.00 | 0.00 |
| Acetone | 0.16 | 0.11 | 0.13 | 0.15 | 0.19 | 0.20 | 0.17 | 0.19 | 0.21 |
| Acrolein | 0.02 | 0.00 | 0.00 | 0.00 | 0.00 | 0.01 | 0.00 | 0.02 | 0.02 |
| Allyl alcohol | 0.00 | 0.00 | 0.00 | 0.00 | 0.00 | 0.00 | 0.00 | 0.00 | 0.00 |
| Allyl acrylate | 0.00 | 0.00 | 0.00 | 0.00 | 0.00 | 0.00 | 0.00 | 0.00 | 0.00 |
| Acetic acid | 2.74 | 3.42 | 2.77 | 2.80 | 2.52 | 2.19 | 3.10 | 2.75 | 2.42 |
| Propionic acid | 0.04 | 0.04 | 0.04 | 0.04 | 0.04 | 0.04 | 0.05 | 0.04 | 0.04 |
| Acrylic acid | 16.06 | 24.30 | 19.19 | 15.15 | 11.46 | 9.12 | 16.65 | 13.41 | 9.91 |
| Carbon monoxide | 4.71 | 6.30 | 5.31 | 4.77 | 3.27 | 2.82 | 4.22 | 3.54 | 2.73 |
| Carbon dioxide | 3.25 | 3.79 | 3.01 | 3.24 | 2.32 | 2.11 | 2.81 | 2.67 | 2.28 |
| Propylene | 3.60 | 3.20 | 3.50 | 3.59 | 3.70 | 3.67 | 3.70 | 3.75 | 3.76 |
| Propane | 69.81 | 59.24 | 65.71 | 70.26 | 76.66 | 79.99 | 68.93 | 73.96 | 78.60 |
| Carbon balance (%) | 100.4 | 100.4 | 99.6 | 100.0 | 100.2 | 100.2 | 99.6 | 100.3 | 100.0 |

| | Test | | | | | | | |
|---|---|---|---|---|---|---|---|---|
| | TC3 | | | TC4 | | | | |
| Conditions in the reaction propane + $O_2$/He—Kr/$H_2O$ | 20/45/45 | | | 30/45/45 | | | | |
| Conditions in regeneration $O_2$/He—Kr/$H_2O$ | 20/45/45 | | | 30/45/45 | | | | |
| Comments | Variation of the duration of the propane pulse in the mixture | | | Variation of the duration of the propane pulse in the mixture | | | | |
| Summary | Flask 5 | Flask 6 | Flask 4 | Flask 3 | Flask 2 | Flask 5 | Flask 6 |
| Number of CYCLES | 8 | 6 | 15 | 15 | 8 | 8 | 7 |
| Duration of the injection of propane | 22.5 | 32.5 | 4.25 | 7.4 | 12.3 | 21.8 | 30.4 |
| Yields (%) | | | | | | | |
| Acetaldehyde | 0.01 | 0.01 | 0.01 | 0.01 | 0.01 | 0.01 | 0.01 |
| Propanaldehyde | 0.00 | 0.00 | 0.00 | 0.00 | 0.00 | 0.00 | 0.00 |
| Acetone | 0.23 | 0.25 | 0.18 | 0.21 | 0.21 | 0.21 | 0.20 |
| Acrolein | 0.02 | 0.02 | 0.02 | 0.02 | 0.02 | 0.01 | 0.02 |
| Allyl alcohol | 0.00 | 0.00 | 0.00 | 0.00 | 0.00 | 0.00 | 0.00 |
| Allyl acrylate | 0.00 | 0.00 | 0.00 | 0.00 | 0.00 | 0.00 | 0.00 |
| Acetic acid | 1.86 | 1.86 | 2.75 | 2.48 | 1.99 | 1.49 | 1.31 |
| Propionic acid | 0.04 | 0.04 | 0.04 | 0.04 | 0.04 | 0.03 | 0.03 |
| Acrylic acid | 6.69 | 6.31 | 13.29 | 10.33 | 7.66 | 5.11 | 4.12 |
| Carbon monoxide | 1.77 | 1.52 | 3.81 | 2.93 | 2.12 | 1.39 | 1.23 |
| Carbon dioxide | 1.64 | 1.39 | 2.90 | 2.49 | 2.00 | 1.36 | 1.18 |
| Propylene | 3.69 | 3.47 | 3.82 | 3.74 | 3.78 | 3.56 | 3.36 |
| Propane | 84.11 | 85.42 | 73.47 | 78.08 | 82.48 | 86.82 | 88.72 |
| Carbon balance (%) | 100.0 | 100.3 | 100.3 | 100.3 | 100.3 | 100.0 | 100.2 |

| | Test | | | | | | | | |
|---|---|---|---|---|---|---|---|---|---|
| | TC1 | | TC2 | | | | TC3 | | |
| Conditions in the reaction propane + $O_2$/He—Kr/$H_2O$ | 10/45/45 | | 10/45/45 | | | | 20/45/45 | | |
| Conditions in regeneration $O_2$/He—Kr/$H_2O$ | 20/45/45 | | 20/45/45 | | | | 20/45/45 | | |
| Comments | Standard test | | Variation of the duration of the propane pulse in the mixture | | | | Variation of the duration of the propane pulse in the mixture | | |
| Summary | Average | Flask 4 | Flask 3 | Flask 2 | Flask 5 | Flask 6 | Flask 4 | Flask 3 | Flask 2 |
| Number of CYCLES | 60 | 15 | 15 | 8 | 8 | 7 | 15 | 15 | 8 |
| Duration of the injection of propane | 12.2 | 4.45 | 7.7 | 12.5 | 22.2 | 31.8 | 4.45 | 7.6 | 12.65 |
| Selectivities (%) | | | | | | | | | |
| Acetaldehyde | 0.09 | 0.00 | 0.00 | 0.00 | 0.00 | 0.06 | 0.00 | 0.06 | 0.06 |
| Propanaldehyde | 0.00 | 0.00 | 0.00 | 0.00 | 0.00 | 0.00 | 0.00 | 0.00 | 0.00 |
| Acetone | 0.53 | 0.27 | 0.37 | 0.52 | 0.82 | 1.01 | 0.56 | 0.74 | 1.01 |
| Acrolein | 0.06 | 0.00 | 0.00 | 0.00 | 0.00 | 0.07 | 0.00 | 0.07 | 0.09 |
| Allyl alcohol | 0.00 | 0.00 | 0.00 | 0.00 | 0.00 | 0.00 | 0.00 | 0.00 | 0.00 |
| Allyl acrylate | 0.00 | 0.00 | 0.00 | 0.00 | 0.00 | 0.00 | 0.00 | 0.00 | 0.00 |
| Acetic acid | 8.97 | 8..30 | 8.15 | 9.40 | 10.71 | 10.87 | 10.11 | 10.42 | 11.31 |
| Propionic acid | 0.14 | 0.09 | 0.11 | 0.13 | 0.18 | 0.19 | 0.15 | 0.16 | 0.19 |
| Acrylic acid | 52.46 | 59.03 | 56.53 | 50.95 | 48.76 | 45.19 | 54.23 | 50.83 | 46.36 |
| Carbon monoxide | 15.38 | 15.31 | 15.65 | 16.03 | 13.92 | 13.98 | 13.73 | 13.41 | 12.75 |
| Carbon dioxide | 10.63 | 9.21 | 8.86 | 10.91 | 9.87 | 10.46 | 9.16 | 10.11 | 10.67 |
| Propylene | 11.76 | 7.78 | 10.32 | 12.06 | 15.73 | 18.16 | 12.06 | 14.21 | 17.57 |
| Quantity of $O_2$ consumed (g O/kg catalyst) | 0.627 | 0.310 | 0.434 | 0.628 | 0.836 | 1.019 | 0.428 | 0.625 | 0.825 |
| µmole propane for 1 cycle | 135.3 | 49.3 | 85.4 | 138.6 | 246.1 | 352.5 | 95.0 | 162.3 | 270.1 |
| Propane conversion ratio | 2783 | 5655 | 3884 | 2759 | 1980 | 1612 | 3854 | 2693 | 1969 |

TABLE 12-continued (kg catalyst/kg converted propane)

|  | Test | | | | | | | |
|---|---|---|---|---|---|---|---|---|
|  | TC3 | | | TC4 | | | | |
| Conditions in the reaction propane + $O_2$/He—Kr/$H_2O$ | 20/45/45 | | | 30/45/45 | | | | |
| Conditions in regeneration $O_2$/He—Kr/$H_2O$ | 20/45/45 | | | 30/45/45 | | | | |
| Comments | Variation of the duration of the propane pulse in the mixture | | | Variation of the duration of the propane pulse in the mixture | | | | |
| Summary | Flask 5 | Flask 6 | Flask 4 | Flask 3 | Flask 2 | Flask 5 | Flask 6 |
| Number of CYCLES | 8 | 6 | 15 | 15 | 8 | 8 | 7 |
| Duration of the injection of propane | 22.5 | 32.5 | 4.25 | 7.4 | 12.3 | 21.8 | 30.4 |
| Selectivities (%) | | | | | | | |
| Acetaldehyde | 0.06 | 0.07 | 0.05 | 0.06 | 0.06 | 0.06 | 0.08 |
| Propanaldehyde | 0.00 | 0.00 | 0.00 | 0.00 | 0.00 | 0.00 | 0.00 |
| Acetone | 1.42 | 1.70 | 0.67 | 0.96 | 1.19 | 1.56 | 1.77 |
| Acrolein | 0.10 | 0.12 | 0.06 | 0.09 | 0.10 | 0.10 | 0.13 |
| Allyl alcohol | 0.00 | 0.00 | 0.00 | 0.00 | 0.00 | 0.00 | 0.00 |
| Allyl acrylate | 0.00 | 0.00 | 0.00 | 0.00 | 0.00 | 0.00 | 0.00 |
| Acetic acid | 11.65 | 12.48 | 10.25 | 11.14 | 11.17 | 11.34 | 11.44 |
| Propionic acid | 0.23 | 0.25 | 0.17 | 0.18 | 0.20 | 0.24 | 0.22 |
| Acrylic acid | 42.00 | 42.43 | 49.54 | 46.43 | 42.99 | 38.75 | 35.95 |
| Carbon monoxide | 11.10 | 10.23 | 14.21 | 13.15 | 11.88 | 10.56 | 10.74 |
| Carbon dioxide | 10.29 | 9.37 | 10.80 | 11.18 | 11.20 | 10.34 | 10.34 |
| Propylene | 23.15 | 23.34 | 14.25 | 16.81 | 21.21 | 27.05 | 29.33 |
| Quantity of $O_2$ consumed (g O/kg catalyst) | 1.033 | 1.363 | 0.548 | 0.776 | 0.993 | 1.220 | 1.454 |
| μmole propane for 1 cycle | 480.5 | 694.0 | 138.0 | 240.3 | 399.5 | 708.0 | 987.3 |
| Propane conversion ratio (kg catalyst/kg converted propane) | 1490 | 1125 | 3108 | 2160 | 1626 | 1220 | 1022 | b) Tests TC5 to TC7

The results are shown in the three tables below.

It is observed that the addition of oxygen at the start of the propane pulse, rather than at the end of the pulse, leads to a small gain in acrylic acid selectivity, which appears to result from a lower $CO_x$ selectivity.

TABLE 13

|  | Test | | | | | | | | | | | |
|---|---|---|---|---|---|---|---|---|---|---|---|---|
|  | TC5 | | | | TC6 | | | | TC7 | | | |
| Conditions in the reaction propane + $O_2$/He—Kr/$H_2O$ | 30 + 30/45/45 | | | | 30 + 30/45/45 | | | | 30 + 30/45/45 | | | |
| Conditions in regeneration $O_2$/He—Kr/$H_2O$ | 20/45/45 | | | | 20/45/45 | | | | 20/45/45 | | | |
| Comments | Variation in the duration of the $O_2$ injection in the propane pulse - $O_2$ injection at the start of the pulse | | | | Variation in the duration of the $O_2$ injection in the propane pulse - $O_2$ injection at the end of the pulse | | | | Duration of the $O_2$ injection in the constant propane pulse - $O_2$ injection at the end of the pulse then at the start of the pulse | | | |
| Summary | Flask 1 | Flask 2 | Flask 3 | Flask 4 | Flask 1 | Flask 2 | Flask 3 | Flask 4 | Flask 1 | Flask 2 | Flask 3 | Flask 4 |
| Number of CYCLES | 10 | 10 | 10 | 10 | 10 | 10 | 10 | 10 | 10 | 10 | 10 | 10 |
| Duration of the injection of propane | 32.6 | 33 | 32.9 | 34 | 34.9 | 35.4 | 34.7 | 33.6 | 33.9 | 34.5 | 33.9 | 34 |
| Duration of the $O_2$ pulses injected into the propane | 5 | 10 | 15 | 20 | 20 | 15 | 10 | 5 | 20 | 20 | 20 | 20 |
| Yields (%) | | | | | | | | | | | | |
| Acetaldehyde | 0.0 | 0.0 | 0.0 | 0.0 | 0.0 | 0.0 | 0.0 | 0.0 | 0.0 | 0.0 | 0.0 | 0.0 |

TABLE 13-continued

| | | | | | | | | | | | | |
|---|---|---|---|---|---|---|---|---|---|---|---|---|
| Propanaldehyde | 0.0 | 0.0 | 0.0 | 0.0 | 0.0 | 0.0 | 0.0 | 0.0 | 0.0 | 0.0 | 0.0 | 0.0 |
| Acetone | 0.2 | 0.2 | 0.2 | 0.2 | 0.1 | 0.1 | 0.2 | 0.2 | 0.1 | 0.1 | 0.2 | 0.2 |
| Acrolein | 0.0 | 0.0 | 0.0 | 0.0 | 0.0 | 0.0 | 0.0 | 0.0 | 0.0 | 0.0 | 0.0 | 0.0 |
| Allyl alcohol | 0.0 | 0.0 | 0.0 | 0.0 | 0.0 | 0.0 | 0.0 | 0.0 | 0.0 | 0.0 | 0.0 | 0.0 |
| Allyl acrylate | 0.0 | 0.0 | 0.0 | 0.0 | 0.0 | 0.0 | 0.0 | 0.0 | 0.0 | 0.0 | 0.0 | 0.0 |
| Acetic acid | 1.6 | 1.8 | 2.0 | 2.0 | 1.8 | 1.6 | 1.6 | 1.5 | 1.9 | 1.9 | 2.0 | 2.0 |
| Propionic acid | 0.0 | 0.0 | 0.0 | 0.0 | 0.0 | 0.0 | 0.0 | 0.0 | 0.0 | 0.0 | 0.0 | 0.0 |
| Acrylic acid | 6.7 | 8.6 | 10.2 | 11.6 | 10.5 | 7.9 | 6.6 | 5.1 | 11.4 | 11.1 | 11.9 | 12.0 |
| Carbon monoxide | 1.8 | 2.1 | 2.4 | 2.7 | 2.9 | 2.4 | 2.0 | 1.7 | 3.1 | 2.9 | 2.8 | 2.9 |
| Carbon dioxide | 1.6 | 1.8 | 2.0 | 2.1 | 2.3 | 2.0 | 1.7 | 1.5 | 2.5 | 2.3 | 2.4 | 2.3 |
| Propylene | 3.6 | 3.9 | 4.1 | 4.2 | 4.1 | 3.9 | 3.7 | 3.4 | 4.1 | 4.2 | 4.2 | 4.3 |
| Propane | 84.4 | 81.5 | 79.0 | 77.3 | 78.2 | 82.2 | 84.1 | 86.6 | 76.5 | 77.6 | 76.4 | 76.1 |
| Carbon balance (%) | 100.1 | 100.0 | 99.9 | 100.2 | 100.1 | 100.2 | 100.0 | 100.1 | 99.8 | 100.1 | 100.0 | 99.8 |

| | Test | | | | | | | | | | | |
|---|---|---|---|---|---|---|---|---|---|---|---|---|
| | TC5 | | | | TC6 | | | | TC7 | | | |
| Conditions in the reaction propane + $O_2$/He—Kr/$H_2O$ | 30 + 30/45/45 | | | | 30 + 30/45/45 | | | | 30 + 30/45/45 | | | |
| Conditions in regeneration $O_2$/He—Kr/$H_2O$ | 20/45/45 | | | | 20/45/45 | | | | 20/45/45 | | | |
| Comments | Variation in the duration of the $O_2$ injection in the propane pulse - $O_2$ injection at the start of the pulse | | | | Variation in the duration of the $O_2$ injection in the propane pulse - $O_2$ injection at the end of the pulse | | | | Duration of the $O_2$ injection in the constant propane pulse - $O_2$ injection at the end of the pulse then at the start of the pulse | | | |
| Summary | Flask 1 | Flask 2 | Flask 3 | Flask 4 | Flask 1 | Flask 2 | Flask 3 | Flask 4 | Flask 1 | Flask 2 | Flask 3 | Flask 4 |
| Number of CYCLES | 10 | 10 | 10 | 10 | 10 | 10 | 10 | 10 | 10 | 10 | 10 | 10 |
| Duration of the injection of propane | 32.6 | 33 | 32.9 | 34 | 34.9 | 35.4 | 34.7 | 33.6 | 33.9 | 34.5 | 33.9 | 34 |
| Duration of the oxygen pulses injected into the propane (s) | 5 | 10 | 15 | 20 | 20 | 15 | 10 | 5 | 20 | 20 | 20 | 20 |
| Selectivities (%) | | | | | | | | | | | | |
| Acetaldehyde | 0.08 | 0.06 | 0.05 | 0.05 | 0.05 | 0.05 | 0.07 | 0.09 | 0.05 | 0.04 | 0.04 | 0.04 |
| Propanaldehyde | 0.00 | 0.00 | 0.00 | 0.00 | 0.00 | 0.00 | 0.00 | 0.00 | 0.00 | 0.00 | 0.00 | 0.00 |
| Acetone | 1.36 | 1.09 | 0.88 | 0.73 | 0.64 | 0.81 | 1.13 | 1.53 | 0.60 | 0.64 | 0.66 | 0.67 |
| Acrolein | 0.13 | 0.11 | 0.10 | 0.10 | 0.10 | 0.10 | 0.13 | 0.14 | 0.11 | 0.11 | 0.10 | 0.10 |
| Allyl alcohol | 0.00 | 0.00 | 0.00 | 0.00 | 0.00 | 0.00 | 0.00 | 0.00 | 0.00 | 0.00 | 0.00 | 0.00 |
| Allyl acrylate | 0.00 | 0.00 | 0.00 | 0.00 | 0.00 | 0.00 | 0.00 | 0.00 | 0.00 | 0.00 | 0.00 | 0.00 |
| Acetic acid | 10.50 | 9.81 | 9.35 | 8.90 | 8.45 | 8.78 | 9.85 | 11.20 | 8.21 | 8.24 | 8.57 | 8.58 |
| Propionic acid | 0.20 | 0.19 | 0.19 | 0.18 | 0.17 | 0.18 | 0.21 | 0.22 | 0.16 | 0.17 | 0.16 | 0.17 |
| Acrylic acid | 42.8 | 46.5 | 49.0 | 50.7 | 48.1 | 43.9 | 41.8 | 37.7 | 48.9 | 49.1 | 50.7 | 50.5 |
| Carbon monoxide | 11.5 | 11.6 | 11.7 | 11.7 | 13.4 | 13.3 | 12.7 | 12.3 | 13.3 | 12.8 | 11.8 | 12.0 |
| Carbon dioxide | 10.2 | 9.6 | 9.4 | 9.3 | 10.4 | 11.1 | 11.0 | 11.4 | 10.9 | 10.4 | 10.0 | 9.9 |
| Propylene | 23.1 | 21.0 | 19.4 | 18.3 | 18.6 | 21.7 | 23.1 | 25.4 | 17.8 | 18.5 | 18.0 | 18.0 |

| | Test | | | | | | | | | | | |
|---|---|---|---|---|---|---|---|---|---|---|---|---|
| | TC5 | | | | TC6 | | | | TC7 | | | |
| Conditions in the reaction propane + $O_2$/He—Kr/$H_2O$ | 30 + 30/45/45 | | | | 30 + 30/45/45 | | | | 30 + 30/45/45 | | | |
| Conditions in regeneration $O_2$/He—Kr/$H_2O$ | 20/45/45 | | | | 20/45/45 | | | | 20/45/45 | | | |
| Comments | Variation in the duration of the $O_2$ injection in the propane pulse - $O_2$ injection at the start of the pulse | | | | Variation in the duration of the $O_2$ injection in the propane pulse - $O_2$ injection at the end of the pulse | | | | Duration of the $O_2$ injection in the constant propane pulse - $O_2$ injection at the end of the pulse then at the start of the pulse | | | |
| Summary | Flask 1 | Flask 2 | Flask 3 | Flask 4 | Flask 1 | Flask 2 | Flask 3 | Flask 4 | Flask 1 | Flask 2 | Flask 3 | Flask 4 |
| Number of CYCLES | 10 | 10 | 10 | 10 | 10 | 10 | 10 | 10 | 10 | 10 | 10 | 10 |
| Duration of the injection of propane | 32.6 | 33 | 32.9 | 34 | 34.9 | 35.4 | 34.7 | 33.6 | 33.9 | 34.5 | 33.9 | 34 |
| Duration of the $0_2$ pulses injected into the propane (s) | 5 | 10 | 15 | 20 | 20 | 15 | 10 | 5 | 20 | 20 | 20 | 20 |
| Quantity of oxygen consumed (g O/Kg catalyst) | 2.25 | 2.69 | 3.08 | 3.52 | 3.53 | 2.91 | 2.47 | 2.00 | 3.67 | 3.56 | 3.62 | 3.66 |
| μmoles of propane for 1 cycle | 1059 | 1072 | 1069 | 1104 | 1133 | 1150 | 1127 | 1091 | 1101 | 1120 | 1101 | 1104 |
| μmoles of $O_2$ added per cycle | 158 | 317 | 475 | 634 | 634 | 475 | 317 | 158 | 634 | 634 | 634 | 634 |

TABLE 13-continued

| μmoles of oxygen consumed (products formed)/cycle | 704 | 843 | 963 | 1101 | 1104 | 911 | 773 | 625 | 1153 | 1119 | 1140 | 1152 |
|---|---|---|---|---|---|---|---|---|---|---|---|---|
| Propane conversion ratio (kg catalyst/kg converted propane) | 681 | 575 | 504 | 467 | 454 | 556 | 623 | 740 | 435 | 457 | 433 | 427 |

Example 12

Figure 2:
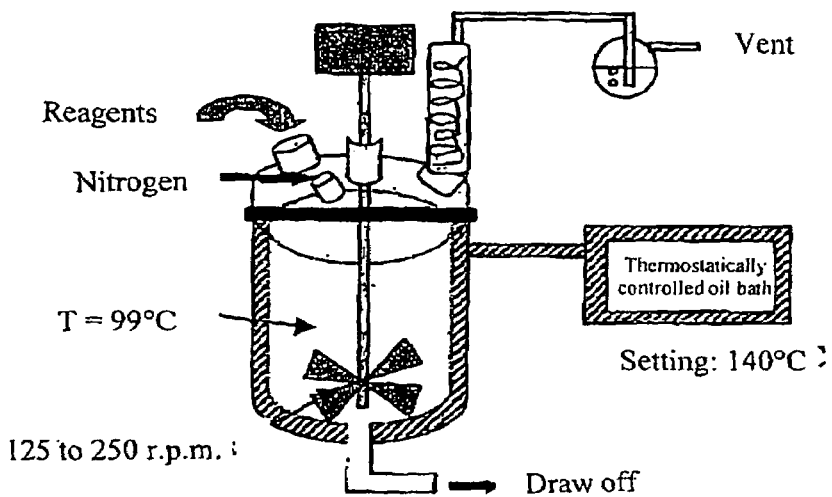
FIG. 2 is a schematic representation of a reactor assembly used in conjunction with an embodiment of the present invention.

Preparation of the Precursor of a Catalyst of Formula: $Mo_1V_{0.3}Sb_{0.15}Nb_{0.1}Si_{0.76}O_x$ Stage 1: Dissolution-precipitation Solution A The assembly illustrated in FIG. 2 is used which comprises a 1 liter reactor of the SVL type equipped with a stirrer connected to a motor and a water cooler containing Raschig rings.

A nitrogen supply is installed on the reactor and a gas washing bottle is placed at the outlet of the cooler. The heating is ensured by a thermostatically controlled oil bath. 12.3 g of ammonium metavanade (AMV) (i.e. 0.1052 mole of vanadium) are placed in solution in 260 ml of demineralised water, in the reactor, under stirring. A yellow solution is obtained. 7.7 g of $Sb_2O_3$ (i.e. 0.0528 mole of antimony) are added to the limpid solution, then 61.8 g of ammonium heptamolybdate (AHM) (i.e. 0.3501 mole of molybdenum) are added. After the addition of AHM, the reactor is placed under nitrogen flow, the reaction is maintained under stirring, at reflux, for 4 hours. A black solution is gradually obtained; the reaction is considered to be complete after 1 hour. The solution obtained is called solution A.

Solution B 6.1 g (0.0532 mole) of an aqueous solution of $H_2O_2$ at 30% by weight is dissolved in 98 g of water, and are then added to solution A over 2 to 3 minutes. The solution becomes limpid orange in 4-5 minutes. Then 40 g of Ludox silica (0.2663 mole of Si) are added in one go and the solution becomes cloudy. The solution formed is called solution B.

Solution C

Solution C is prepared at the same time as solution A: 13.2 g (0.1047 mole) of oxalic acid and 5.9 g of niobic acid (i.e. 0.0351 mole of Nb) are dissolved under stirring at 80° C., in 100 g of water, over 2 hours. This solution is then centrifuged at 6200 r.p.m. for 12 minutes, in order to obtain a limpid solution C.

Then, solution C is added to solution B, in one go. A fluid gel is obtained which is orange then yellow. Stirring is continued for 30 minutes under nitrogen flow, under reflux.

2) Stage 2: Drying

The gel obtained previously is dried in a ventilated oven, on Teflon-covered plates, overnight, at 130° C. 104.2 g of dry precursor are recovered. This precursor, hereafter called P1, is in the form of sheets, black on the top with a green film underneath Example 13

Preparation of the Precursors P2 to P15

The process is carried out as indicated in Example 12, except for the conditions shown in the following Table 14, in which the appearances of the precursors obtained are also shown.

TABLE 14

Summary of the precursor synthesis

| | | Solution A | | Solution B: addition of oxygenated water | | |
|---|---|---|---|---|---|---|
| Precursor | Mounting | Sb/Mo | Duration of stirring of solution (Mo, V, Sb) in hours | $H_2O_2$/Mo | Time of introduction of $H_2O_2$ | Colour change |
| P2 | Three necked flask with magnetic stirrer | 0.15 | 5 | 0.15 diluted | 5 h | orange |
| P3 | SVL | 0.15 | 5 | 0.15 diluted | 2 mn | orange |
| P4 | SVL | 0.15 | 3 | 0.15 diluted | 2–3 mn | orange in 5 mn |
| P5 | SVL | 0.15 | 2 | 0.15 diluted | 2–3 mn | orange in 5–7 mn |
| P1 | SVL | 0.15 | 4 | 0.15 diluted | 2–3 mn | orange in 2–3 mn |
| P6 | SVL | 0.15 | 5 | 0.15 diluted | 2–3 mn | orange in 4–5 mn |
| P7 | SVL | 0.15 | 4 | 0.15 diluted | | orange in 2–3 mn |
| P8 | SVL | 0.23 | 4 | 0.23 diluted | In two goes | cloudy orange |
| P9 | SVL | 0.23 | 4 | 0.23 diluted | 1–2 minutes | brown green |
| P10 | SVL | 0.23 | 5 | 0.23 diluted | NA | black dark purple |

TABLE 14-continued

| Summary of the precursor synthesis | | | | | |
|---|---|---|---|---|---|
| P11 | SVL | 0.15 | 4 | 0.15 diluted | orange in 5 minutes |
| P12 | SVL | 0.15 | 4 | 0.15 diluted | Orange |
| P13 | SVL | 0.15 | 4 | 0.15 diluted | Orange |
| P14 | SVL | 0.23 | 4 | 0.23 diluted | slow, orange |
| P15 | SVL | 0.15 | 4 | 0.15 diluted | slow, orange |

| | Solution B: addition of oxygenated water | | | Solution C | Appearance of |
|---|---|---|---|---|---|
| Precursor | Limpidity | Remark | Si/Mo | Remark | precursor |
| P2 | No | yellow precipitate | 0.76 | | black, green underneath |
| P3 | Yes | transferred to a heated three-necked flask before introduction of $H_2O_2$, still limpid | 0.76 | | black with some traces of green |
| P4 | Yes | transferred to a heated three-necked flask before introduction of $H_2O_2$ | 0.76 | Ox/Mo: 0.28 | black |
| P5 | Yes | transferred to a heated three-necked flask before introduction of $H_2O_2$ | 0.76 | Ox/Mo: 0.28 | black |
| P1 | Yes | no transfer | 0.76 | | black |
| P6 | Yes | | 0.76 | Heated for 1 h30 | |
| P7 | Yes | | 0.76 | | black, green underneath |
| P8 | no | + a few drops of $H_2O_2$ | 0.76 | | black, green underneath |
| P9 | no | | 0.76 | | black, green underneath |
| P10 | no | addition of $H_2O_2$ in solution C | 0.76 | solution C added directly before the silica | black, finer than usual |
| P11 | yes | | 0.76 | no niobium, heated to 30° C. | black, dark khaki green underneath |
| P12 | Yes | + a few drops of $H_2O_2$ | 0.76 | | |
| P13 | yes, then cloudy | new bottle, same batch + 20 drops $H_2O_2$ | 0.76 | heated for 1h15 | black, green underneath, entirely green area |
| P14 | yes | +20 drops of $H_2O_2$ | 0.76 | | fine black, green underneath |
| P15 | yes | +2 drops of $H_2O_2$ | 0.93 | new batch of oxalic acid | black with yellow parts |

Example 14

Precalcination and Calcination of the Precursors P1 to P15

Figure 3:
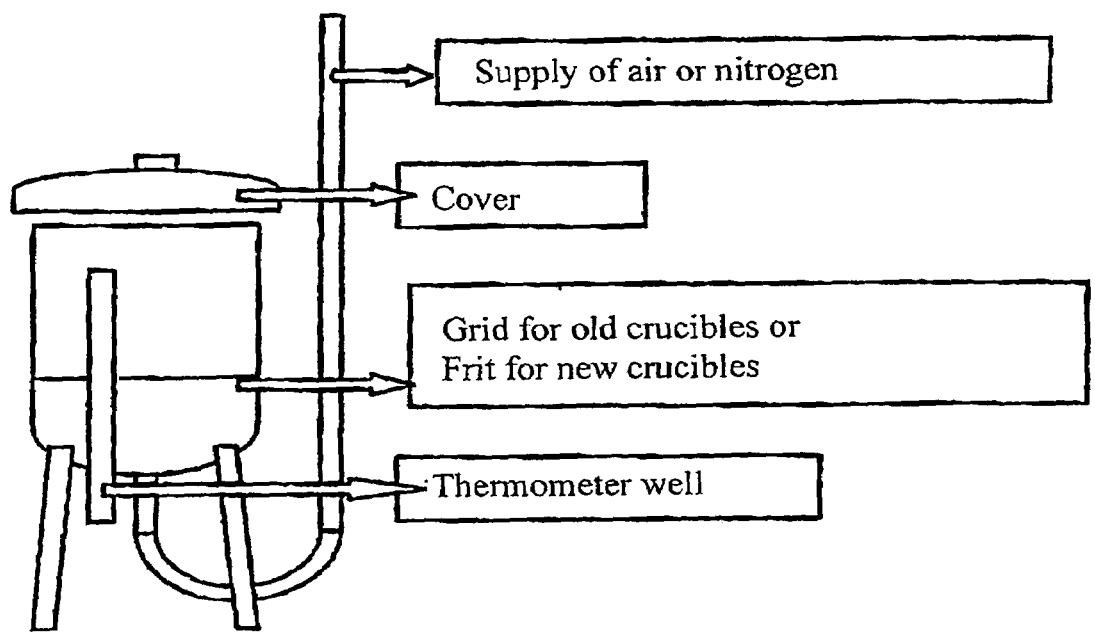
FIG. 3 is a schematic representation of a muffle furnace for a steel capacitor used in conjunction with an embodiment of the present invention.

The precalcinations and the calcinations are carried out in combustion boats under flow of air and of nitrogen respectively, in steel capacitors. These capacitors are directly installed in muffle furnaces and the air or nitrogen is supplied via the flue. An internal thermometer well allows precise monitoring of the temperature. The cover prevents air returning towards the catalyst (see FIG. 3).

The precursors P1 to P15 obtained in Examples 12 and 13 are precalcinated at 300° C., for 4 hours, under air flow, then calcinated at 600° C., for 2 hours under nitrogen flow of 50 ml/mn/g in a muffle furnace. The calcinations The following conditions for heat treatment of the precursors are studied:
  calciner;
  flow rate of precalcination air in ml/min/g;
  calcination temperature variation gradient in ° C./min.

These conditions are shown in Table 15 below.

TABLE 15

| Heat treatment of the precursors (for weights of 25 to 30 g) | | | | | | |
|---|---|---|---|---|---|---|
| | | Precalcination flow | Calcination slopes under $N_2$ (° C./min) | | | |
| Catalyst | Precursor | rate (ml/min/g) | 1 | 2 | 5 | 10 |
| C2 | P2 | 50.4 | | ■ | | |
| C3 | P3 | 47 | | ■ | | |
| C4 | P4 | 47 | | ■ | | |
| C5 | P5 | 47 | | ■ | | |
| C1 | P1 | 48.5 | | ■ | | |
| C6 | P6 | 45.8 | | | ■ | ■ |

TABLE 15-continued

Heat treatment of the precursors (for weights of 25 to 30 g)

| Catalyst | Precursor | Precalcination flow rate (ml/min/g) | Calcination slopes under $N_2$ (° C./min) 1 | 2 | 5 | 10 |
|---|---|---|---|---|---|---|
| C7  | P7  | 44.9  | ■ |   |   |   |
| C8  | P7  | 45    |   | ■ |   |   |
| C9  | P7  | 47.2  |   |   | ■ |   |
| C10 | P7  | 47    |   |   |   | ■ |
| C11 | P7  | 0     |   | ■ |   |   |
| C12 | P7  | 10    |   | ■ |   |   |
| C13 | P7  | 20.1  |   | ■ |   |   |
| C14 | P7  | 51.6  |   | ■ |   |   |
| C15 | P8  | 46.9  | ■ |   |   |   |
| C16 | P8  | 47.1  |   | ■ |   |   |
| C17 | P8  | 45.5  |   |   | ■ |   |
| C18 | P8  | 48    |   |   |   | ■ |
| C19 | P8  | 21.15 |   |   |   | ■ |
| C20 | P8  | 10.55 |   |   |   | ■ |
| C21 | P8  | 20.9  |   |   | ■ |   |
| C22 | P8  | 10.5  |   |   | ■ |   |
| C23 | P9  | 45.2  |   | ■ |   |   |
| C24 | P10 | 47.2  |   | ■ |   |   |
| C25 | P11 | 46    |   | ■ |   |   |
| C26 | P12 | 45.7  |   | ■ |   |   |
| C27 | P13 | 47.5  |   | ■ |   |   |
| C28 | P14 | 47    |   | ■ |   |   |
| C29 | P15 | 50.7  |   | ■ |   |   |
| C30 | P15 | 50.3  |   | ■ |   |   |
| C31 | P15 | 34.8  |   | ■ |   |   |
| C32 | P15 | 18.7  |   | ■ |   |   |

Example 15

Tests of the Catalysts Obtained a) Apparatus

In order to simulate the process according to the invention, simulations were carried out in the laboratory in a laboratory fixed bed reactor.

The following are therefore loaded from the bottom to the top of a vertical reactor with cylindrical shape and made of pyrex:
- a first height of 1 ml of silicon carbide in the form of particles of 0.125 mm in diameter,
- a second height of 5 g of catalyst in the form of particles of 0.02 to 1 mm diluted with 10 ml of silicon carbide in the form of particles of 0.125 mm in diameter,
- a third height of 1 ml of silicon carbide in the form of particles of 0.125 mm in diameter, and
- a fourth height of silicon carbide in the form of particles of 1.19 mm in diameter, so as to fill all of the reactor.

b) Test Conditions

The catalyst is simultaneously supplied with propane and with oxygen. The helium acts as diluent gas and water is vaporized in the gaseous flow.

The catalysts are tested at 380° C., 390° C. and 400° C. with a ratio propane/$O_2$/He—Kr/$H_2O$ of 10/10/45/45. The total flow rate of the gaseous flow rises to 8.65 Nl/h.

The reactor is placed in an isothermal furnace. It is supplied with propane, oxygen and helium by mass flowmeters. An HPLC pump and a vaporizer ensure the production of vapor.

Thermocouples are placed in the furnace to allow their regulation, and in the reactor to measure the "hot spot", i.e. the highest temperature in the catalyst bed.

c) Results of the Tests

Only the results of the tests carried out at 400° C. are given. It is at this temperature that it was observed that the best results were generally obtained.

The results of the tests are recorded in Tables 16 and 17 below in which the yields are only calculated on the basis of the routine chromatographic analyses. The selectivities are calculated as being the yield of a given product over the sum of the yields of products.

The carbon balances are used to ensure the homogeneity of the data. They are considered to be acceptable for values comprises between 95 and 105%.

The yield calculations are based on the krypton content of the gas. Measurement of the flow rate of dry gas at the outlet of the reactor allows calculations to be made based on this flow rate of gas. The yield calculations can thus be validated.

The yields and selectivities of each of the products assayed are given, as well as the yield of acid, obtained by assay with 0.1N soda. This is a pseudo-yield obtained supposing that all the acids formed have 3 carbon atoms.

TABLE 16

Summary table of the yields produced by the catalysts
Yields - TTUc (%)

| Catalyst | Reaction temp (° C.) | Hotspot temp. (° C.) | TTG (ΣTTU) | TTG $O_2$ (ΣTTU) | Carbon balance | Oxygen balance | Acetaldehyde | Propanaldehyde | Acetone |
|---|---|---|---|---|---|---|---|---|---|
| C5 | 400 | 413   | 19.5 | 42.8 | 100.9 | 101.6 | 0.0 | 0.0 | 0.1 |
| C4 | 400 | 417   | 18.2 | 41.4 | 97.2  | 99.1  | 0.0 | 0.0 | 0.1 |
| C1 | 400 | 413.6 | 16.9 | 36.4 | 100.3 | 100.2 | 0.0 | 0.0 | 0.1 |
| C3 | 400 | 411.9 | 18.3 | 38.9 | 101.0 | 100.8 | 0.0 | 0.0 | 0.1 |

TABLE 16-continued

Summary table of the yields produced by the catalysts
Yields - TTUc (%)

| Catalyst | | | | | | | | | | |
|---|---|---|---|---|---|---|---|---|---|---|
| C2  | 400 | 410   | 16.0 | 32.5 | 99.3  | 99.1  | 0.0 | 0.0 | 0.2 |
| C6  | 400 | 424   | 20.4 | 47.6 | 102.5 | 99.7  | 0.0 | 0.0 | 0.1 |
| C7  | 400 | 411   | 17.3 | 35.5 | 100.2 | 100.4 | 0.0 | 0.0 | 0.1 |
| C8  | 400 | 409.3 | 16.1 | 33.0 | 99.2  | 94.1  | 0.0 | 0.0 | 0.1 |
| C9  | 400 | 416   | 16.1 | 34.0 | 104.3 | 99.9  | 0.0 | 0.0 | 0.2 |
| C10 | 400 | 420   | 19.1 | 41.6 | 103.3 | 100.0 | 0.0 | 0.0 | 0.2 |
| C12 | 400 | 410.7 | 15.7 | 32.2 | 97.3  | 97.5  | 0.0 | 0.0 | 0.1 |
| C14 | 400 | 405.2 | 17.7 | 36.5 | 99.3  | 99.6  | 0.0 | 0.0 | 0.3 |
| C26 | 400 | 411   | 17.0 | 36.1 | 99.4  | 99.8  | 0.0 | 0.0 | 0.1 |
| C30 | 400 | 409.5 | 13.5 | 25.5 | 99.4  | 99.8  | 0.0 | 0.0 | 0.1 |
| C32 | 400 | 410   | 17.0 | 32.3 | 99.9  | 99.8  | 0.0 | 0.0 | 0.1 |
| C23 | 400 | 410   | 15.6 | 29.6 | 100.6 | 100.9 | 0.0 | 0.0 | 0.1 |
| C16 | 400 | 408.8 | 13.3 | 25.3 | 101.0 | 98.7  | 0.0 | 0.0 | 0.1 |
| C17 | 400 | 411.1 | 20.3 | 42.9 | 99.2  | 98.9  | 0.0 | 0.0 | 0.2 |
| C18 | 400 | 411.1 | 20.1 | 42.5 | 99.0  | 98.5  | 0.0 | 0.0 | 0.2 |
| C28 | 400 | 410   | 16.6 | 33.5 | 102.9 | 98.8  | 0.0 | 0.0 | 0.1 |
| C25 | 400 | 405   | 3.9  | 4.9  | 98.9  | 99.8  | 0.0 | 0.0 | 0.0 |
| C24 | 400 | 401.8 | 12.3 | 21.1 | 106.4 | 104.3 | 0.0 | 0.0 | 1.2 |
| C27 | 400 | 410.4 | 16.0 | 31.1 | 99.6  | 99.8  | 0.0 | 0.0 | 0.1 |

| Catalyst | Acrolein | Allyl alcohol | Allyl acrylate | Acetic acid | Propionic acid | Acrylic acid | CO | $CO_2$ | Propylene | Propane | CO + $CO_2$ | Acid per assay |
|---|---|---|---|---|---|---|---|---|---|---|---|---|
| C5  | 0.0 | 0.0 | 0.0 | 2.4 | 0.1 | 7.3 | 2.8 | 2.2 | 4.6 | 81.4 | 5.0 | 10.1 |
| C4  | 0.0 | 0.0 | 0.0 | 2.3 | 0.1 | 6.5 | 3.0 | 2.1 | 4.0 | 78.9 | 5.2 | 10.2 |
| C1  | 0.0 | 0.0 | 0.0 | 1.7 | 0.1 | 6.1 | 2.5 | 1.8 | 4.4 | 83.4 | 4.3 | 9.1  |
| C3  | 0.0 | 0.0 | 0.0 | 2.0 | 0.1 | 7.4 | 2.4 | 1.8 | 4.6 | 82.7 | 4.2 | 9.9  |
| C2  | 0.1 | .0  | 0.0 | 1.5 | 0.1 | 6.6 | 1.9 | 1.4 | 4.2 | 83.3 | 3.3 | 8.7  |
| C6  | 0.0 | 0.0 | 0.0 | 2.3 | 0.1 | 7.0 | 3.6 | 2.7 | 4.5 | 82.1 | 6.4 | 10.6 |
| C7  | 0.0 | 0.0 | 0.0 | 1.7 | 0.0 | 7.3 | 2.1 | 1.5 | 4.5 | 82.9 | 3.6 | 9.7  |
| C8  | 0.0 | 0.0 | 0.0 | 1.6 | 0.1 | 6.1 | 2.1 | 1.5 | 4.5 | 83.1 | 3.6 | 8.7  |
| C9  | 0.0 | 0.0 | 0.0 | 1.7 | 0.1 | 5.9 | 2.2 | 1.7 | 4.3 | 88.2 | 3.9 | 8.8  |
| C10 | 0.0 | 0.0 | 0.0 | 2.0 | 0.1 | 7.7 | 2.8 | 2.0 | 4.3 | 84.2 | 4.8 | 10.6 |
| C12 | 0.0 | 0.0 | 0.0 | 1.6 | 0.1 | 5.6 | 2.1 | 1.5 | 4.7 | 81.6 | 3.6 | 8.2  |
| C14 | 0.0 | 0.0 | 0.0 | 1.9 | 0.2 | 7.7 | 2.1 | 1.5 | 4.1 | 81.5 | 3.6 | 10.1 |
| C26 | 0.0 | 0.0 | 0.0 | 1.9 | 0.1 | 6.9 | 2.3 | 1.6 | 4.1 | 82.5 | 3.9 | 9.9  |
| C30 | 0.0 | 0.0 | 0.0 | 1.1 | 0.0 | 6.1 | 1.3 | 0.9 | 4.0 | 85.9 | 2.2 | 7.9  |
| C32 | 0.1 | 0.0 | 0.0 | 1.1 | 0.1 | 9.0 | 1.4 | 0.9 | 4.3 | 82.9 | 2.3 | 10.8 |
| C23 | 0.0 | 0.0 | 0.0 | 1.2 | 0.1 | 7.5 | 1.4 | 1.0 | 4.4 | 85.0 | 2.4 | 8.9  |
| C16 | 0.1 | 0.0 | 0.0 | 1.0 | 0.1 | 5.6 | 1.4 | 0.9 | 4.0 | 87.8 | 2.4 | 7.5  |
| C17 | 0.1 | 0.0 | 0.0 | 1.8 | 0.1 | 9.7 | 2.4 | 1.8 | 4.2 | 78.9 | 4.2 | 12.3 |
| C18 | 0.0 | 0.0 | 0.0 | 1.8 | 0.1 | 9.6 | 2.4 | 1.8 | 4.2 | 78.9 | 4.2 | 12.3 |
| C28 | 0.0 | 0.0 | 0.0 | 1.4 | 0.1 | 7.4 | 1.9 | 1.4 | 4.4 | 86.4 | 3.2 | 9.4  |
| C25 | 0.0 | 0.0 | 0.0 | 0.2 | 0.0 | 0.6 | 0.3 | 0.2 | 2.5 | 95.0 | 0.4 | 1.0  |
| C24 | 0.1 | 0.0 | 0.0 | 0.6 | 0.1 | 5.9 | 0.7 | 0.5 | 3.3 | 94.1 | 1.2 | 7.4  |
| C27 | 0.0 | 0.0 | 0.0 | 1.4 | 0.1 | 7.4 | 1.6 | 1.1 | 4.3 | 83.6 | 2.7 | 9.6  |

TABLE 17

Summary table of the selectivities of the catalysts
Selectivities (%)

| Catalyst | Reaction temp (° C.) | Hotspot temp. (° C.) | TTG (Total TTU) | TTG $O_2$ (Total TTU) | Carbon balance | Oxygen balance | Acetaldehyde | Propanaldehyde |
|---|---|---|---|---|---|---|---|---|
| C5  | 400 | 413   | 19.5 | 42.8 | 100.9 | 101.6 | 0.0 | 0.0 |
| C4  | 400 | 417   | 18.2 | 41.4 | 97.2  | 99.1  | 0.1 | 0.0 |
| C1  | 400 | 413.6 | 16.9 | 36.4 | 100.3 | 100.2 | 0.0 | 0.0 |
| C3  | 400 | 411.9 | 18.3 | 38.9 | 101.0 | 100.8 | 0.0 | 0.0 |
| C2  | 400 | 410   | 16.0 | 32.5 | 99.3  | 99.1  | 0.3 | 0.0 |
| C6  | 400 | 424   | 20.4 | 47.6 | 102.5 | 99.7  | 0.0 | 0.0 |
| C7  | 400 | 411   | 17.3 | 35.5 | 100.2 | 100.4 | 0.0 | 0.0 |
| C8  | 400 | 409.3 | 16.1 | 33.0 | 99.2  | 94.1  | 0.0 | 0.0 |
| C9  | 400 | 416   | 16.1 | 34.0 | 104.3 | 99.9  | 0.0 | 0.0 |
| C10 | 400 | 420   | 19.1 | 41.6 | 103.3 | 100.0 | 0.0 | 0.0 |
| C12 | 400 | 410.7 | 15.7 | 32.2 | 97.3  | 97.5  | 0.0 | 0.0 |
| C14 | 400 | 405.2 | 17.7 | 36.5 | 99.3  | 99.6  | 0.0 | 0.0 |
| C26 | 400 | 411   | 17.0 | 36.1 | 99.4  | 99.8  | 0.0 | 0.0 |
| C30 | 400 | 409.5 | 13.5 | 25.5 | 99.4  | 99.8  | 0.1 | 0.0 |
| C32 | 400 | 410   | 17.0 | 32.3 | 99.9  | 99.8  | 0.0 | 0.0 |

TABLE 17-continued

Summary table of the selectivities of the catalysts
Selectivities (%)

| Catalyst | | | | | | | | | |
|---|---|---|---|---|---|---|---|---|---|
| C23 | 400 | 410 | 15.6 | 29.6 | 100.6 | 100.9 | 0.0 | 0.0 | |
| C16 | 400 | 408.8 | 13.3 | 25.3 | 101.0 | 98.7 | 0.0 | 0.0 | |
| C17 | 400 | 411.1 | 20.3 | 42.9 | 99.2 | 98.9 | 0.0 | 0.0 | |
| C18 | 400 | 411.1 | 20.1 | 42.5 | 99.0 | 98.5 | 0.0 | 0.0 | |
| C28 | 400 | 410 | 16.6 | 33.5 | 102.9 | 98.8 | 0.0 | 0.0 | |
| C25 | 400 | 405 | 3.9 | 4.9 | 98.9 | 99.8 | 0.1 | 0.1 | |
| C24 | 400 | 401.8 | 12.3 | 21.1 | 106.4 | 104.3 | 0.0 | 0.0 | |
| C27 | 400 | 410.4 | 16.0 | 31.1 | 99.6 | 99.8 | 0.0 | 0.0 | |

| Catalyst | Acetone | Acrolein | Allyl alcohol | Allyl acrylate | Acetic acid | Propionic acid | Acrylic acid | CO | $CO_2$ | Propylene |
|---|---|---|---|---|---|---|---|---|---|---|
| C5 | 0.6 | 0.1 | 0.0 | 0.0 | 12.5 | 0.5 | 37.2 | 14.4 | 11.0 | 23.6 |
| C4 | 0.8 | 0.2 | 0.0 | 0.0 | 12.6 | 0.4 | 35.6 | 16.7 | 11.7 | 21.8 |
| C1 | 0.7 | 0.1 | 0.0 | 0.0 | 10.4 | 10.4 | 10.4 | 10.4 | 10.4 | 10.4 |
| C3 | 0.7 | 0.1 | 0.0 | 0.0 | 10.7 | 0.3 | 40.3 | 13.3 | 9.8 | 24.9 |
| C2 | 1.0 | 0.5 | 0.0 | 0.0 | 9.2 | 0.8 | 41.2 | 12.1 | 8.6 | 26.3 |
| C6 | 0.7 | 0.2 | 0.0 | 0.0 | 11.3 | 0.3 | 34.4 | 17.8 | 133 | 21.8 |
| C7 | 0.8 | 0.1 | 0.0 | 0.0 | 9.6 | 0.3 | 42.1 | 12.2 | 8.8 | 26.2 |
| C8 | 0.9 | 0.2 | 0.1 | 0.1 | 10.0 | 0.4 | 37.8 | 13.2 | 9.3 | 28.0 |
| C9 | 1.2 | 0.1 | 0.0 | 0.0 | 10.4 | 0.5 | 37.0 | 13.5 | 10.7 | 26.5 |
| C10 | 0.8 | 0.1 | 0.0 | 0.0 | 10.6 | 0.4 | 40.6 | 14.5 | 10.5 | 22.5 |
| C12 | 0.9 | 0.2 | 0.0 | 0.0 | 10.3 | 0.4 | 35.4 | 13.4 | 9.8 | 29.7 |
| C14 | 1.6 | 0.0 | 0.0 | 0.0 | 10.7 | 1.0 | 43.2 | 11.6 | 8.5 | 23.4 |
| C26 | 0.7 | 0.1 | 0.0 | 0.0 | 11.2 | 0.3 | 40.9 | 13.6 | 9.4 | 23.9 |
| C30 | 0.6 | 0.1 | 0.0 | 0.0 | 8.2 | 0.3 | 45.0 | 9.6 | 6.3 | 29.8 |
| C32 | 0.8 | 0.1 | 0.0 | 0.0 | 6.7 | 0.4 | 52.8 | 8.1 | 5.5 | 25.6 |
| C23 | 0.6 | 0.1 | 0.0 | 0.0 | 7.4 | 0.3 | 48.0 | 9.0 | 6.3 | 28.2 |
| C16 | 0.7 | 0.4 | 0.0 | 0.0 | 7.7 | 0.6 | 42.4 | 10.6 | 7.1 | 30.5 |
| C17 | 0.9 | 0.4 | 0.0 | 0.0 | 8.7 | 0.7 | 47.8 | 11.9 | 8.8 | 20.8 |
| C18 | 0.9 | 0.0 | 0.0 | 0.0 | 8.8 | 0.7 | 47.6 | 12.1 | 8.9 | 21.0 |
| C28 | 0.7 | 0.1 | 0.0 | 0.0 | 8.2 | 0.4 | 44.9 | 11.2 | 8.2 | 26.3 |
| C25 | 1.0 | 0.4 | 0.1 | 0.0 | 5.9 | 0.6 | 16.6 | 7.0 | 4.0 | 64.1 |
| C24 | 9.9 | 0.4 | 0.0 | 0.0 | 4.9 | 0.5 | 47.9 | 5.5 | 4.3 | 26.6 |
| C27 | 0.8 | 0.2 | 0.0 | 0.0 | 8.5 | 0.4 | 46.1 | 10.0 | 6.9 | 27.2 |

Example 16

Precursors P16 of the catalyst of formula $Mo_1V_{0.3}Sb_{0.15}Nb_{0.1}Si_{0.76}O_x$ are prepared according to the operating process given in Example 12.

From these precursors P16, a series of catalysts is prepared which are tested.

The precalcination and calcination conditions of the precursor P16 are shown in Tables 18 and 19 below.

1) Stage 1: Dissolution-precipitation

Solution A

The assembly illustrated in FIG. 2 is used which comprises a 1 liter reactor of the SVL type equipped with a stirrer connected to a motor and a water cooler containing Raschig rings. A nitrogen supply is installed on the reactor and a gas washing bottle is placed at the outlet of the cooler. The heating is ensured by a thermostatically controlled oil bath.

30.75 g of ammonium metavanade (AMV) (i.e. 0.2629 mole of vanadium) is placed in solution in 650 ml of demineralised water, in the reactor, under stirring.

A yellow solution is obtained. 19.25 g of $Sb_2O_3$ (i.e. 0.1321 mole of antimony) are added, with 154.5 g of ammonium heptamolybdate (AHM) (i.e. 0.8753 mole of molybdenum) are added. After the addition, the reactor is placed under nitrogen flow, the reaction is maintained under stirring, at reflux, for 4 hours. A black solution is gradually obtained; the reaction is considered to be complete after 1 hour.

The solution obtained is called solution A.

Solution B 15.25 g (0.1346 mole) of an aqueous solution of $H_2O_2$ 30% by weight is dissolved in 90 g of water, and is then added to solution A over 5 minutes. The solution becomes limpid orange in 4-5 minutes. Then 100 g of Ludox AS 40® silica (0.6667 mole of Si) is added in one go and the solution becomes slightly cloudy. The solution formed is called solution B.

Solution C

Solution C is prepared at the same time as solution A: 33.0 g (0.2618 mole) of oxalic acid and 14.75 g of niobic acid (i.e. 0.0877 mole of Nb) are dissolved under stirring at 66° C., in 250 g of water, over 2 hours. This solution is then centrifuged at 6200 r.p.m. for 12 minutes, in order to obtain a limpid solution C.

Then, solution C is added to solution B, in one go. A fluid gel is obtained which is orange then yellow. Stirring is continued for 30 minutes under nitrogen flow, under reflux.

2) Stage 2: Drying

The gel obtained previously is dried in a ventilated oven, on Teflon-covered plates, overnight, at 130° C. 259 g of dry precursor are recovered. This precursor is in the form of sheets, black on the top with a green film underneath.

Thus the precursor is obtained which is hereafter called P16.

Table 18 shows the yields of carbon (TTUc), with $TTG_C = \Sigma TTU_C$ and $TTG_{O2} = \Sigma TTU_O$, the acidities measured by assay with soda, the carbon and oxygen balances.

Table 19 shows the carbon selectivities.

TABLE 18

Yields of the products obtained during the catalyst tests
Yields - TTUc (%)

| Catalyst | Calcination temp (° C.) | Flow rate of air (ml/mn/gca) | Oven temperature (° C.) | Hot temperature (° C.) | TTG = total TTU | TTG O$_2$ = total TTU |
|---|---|---|---|---|---|---|
| C33 | 280 | 0 | 400 | 412 | 16.5 | 35.0 |
| C34 | 280 | 10.6 | 400 | 411 | 15.6 | 31.6 |
| C35 | 290 | 0 | 400 | 412 | 16.5 | 34.5 |
| C36 | 290 | 10.6 | 400 | 411 | 15.5 | 30.9 |
| C37 | 300 | 0 | 400 | 410 | 14.4 | 28.1 |
| C38 | 300 | 10 | 400 | 411 | 15.7 | 32.2 |
| C39 | 300 | 20.1 | 400 | 413 | 16.7 | 34.4 |
| C40 | 300 | 51.6 | 400 | 405 | 17.7 | 36.5 |
| C41 | 320 | 0 | 400 | 414 | 23.5 | 48.7 |
| C42 | 320 | 0 | 420 | 438 | 29.6 | 67.3 |
| C43 | 320 | 10 | 400 | 414 | 21.6 | 44.2 |
| C44 | 280 | 21.2 | 400 | 413 | 20.5 | 45.6 |
| C45 | 290 | 19.1 | 400 | 414 | 16.9 | 35.7 |
| C46 | 320 | 19.2 | 400 | 413 | 18.1 | 39.4 |
| C47 | 280 | 49.2 | 400 | 415 | 18.3 | 39.8 |
| C48 | 290 | 52.9 | 400 | 414 | 20.9 | 46.7 |
| C49 | 320 | 51.6 | 400 | 412 | 16.1 | 36.2 |

| Catalyst | C balance | O balance | Acetaldehyde | Propanaldehyde | Acetone | Acrolein | Allyl alcohol | Allyl acrylate |
|---|---|---|---|---|---|---|---|---|
| C33 | 98.4 | 102.1 | 0.0 | 0.0 | 0.1 | 0.0 | 0.0 | 0.0 |
| C34 | 98.8 | 103.2 | 0.0 | 0.0 | 0.1 | 0.0 | 0.0 | 0.0 |
| C35 | 99.3 | 103.0 | 0.0 | 0.0 | 0.1 | 0.0 | 0.0 | 0.0 |
| C36 | 98.2 | 102.1 | 0.0 | 0.0 | 0.1 | 0.0 | 0.0 | 0.0 |
| C37 | 99.6 | 98.1 | 0.0 | 0.0 | 0.1 | 0.1 | 0.0 | 0.0 |
| C38 | 97.3 | 97.5 | 0.0 | 0.0 | 0.1 | 0.0 | 0.0 | 0.0 |
| C39 | 98.1 | 101.6 | 0.0 | 0.0 | 0.1 | 0.0 | 0.0 | 0.0 |
| C40 | 99.3 | 99.6 | 0.0 | 0.0 | 0.3 | 0.0 | 0.0 | 0.0 |
| C41 | 99.5 | 103.1 | 0.0 | 0.0 | 0.2 | 0.0 | 0.0 | 0.0 |
| C42 | 98.7 | 101.6 | 0.0 | 0.0 | 0.1 | 0.0 | 0.0 | 0.0 |
| C43 | 00.0 | 102.5 | 0.0 | 0.0 | 0.2 | 0.0 | 0.0 | 0.0 |
| C44 | 99.5 | 101.8 | 0.0 | 0.0 | 0.2 | 0.0 | 0.0 | 0.0 |
| C45 | 96.3 | 95.8 | 0.0 | 0.0 | 0.0 | 0.0 | 0.0 | 0.0 |
| C46 | 99.2 | 95.7 | 0.0 | 0.0 | 0.0 | 0.0 | 0.0 | 0.0 |
| C47 | 101.1 | 99.9 | 0.0 | 0.0 | 0.1 | 0.0 | 0.0 | 0.0 |
| C48 | 99.1 | 01.8 | 0.0 | 0.0 | 0.1 | 0.0 | 0.0 | 0.0 |
| C49 | 98.0 | 99.1 | 0.0 | 0.0 | 0.1 | 0.0 | 0.0 | 0.0 |

| Catalyst | Acetic acid | Propionic acid | Acrylic acid | CO | CO$_2$ | Propene | Propane | CO + CO$_2$ | Acid per assay |
|---|---|---|---|---|---|---|---|---|---|
| C33 | 1.9 | 0.1 | 5.3 | 2.6 | 1.9 | 4.6 | 81.9 | 4.5 | 8.3 |
| C34 | 1.5 | 0.1 | 5.8 | 2.0 | 1.5 | 4.5 | 83.2 | 3.6 | 8.1 |
| C35 | 1.7 | 0.1 | 5.7 | 2.4 | 1.8 | 4.6 | 82.7 | 4.2 | 8.3 |
| C36 | 1.5 | 0.1 | 6.0 | 2.0 | 1.4 | 4.5 | 82.7 | 3.4 | 8.2 |
| C37 | 1.2 | 0.1 | 5.5 | 1.7 | 1.3 | 4.5 | 85.2 | 2.9 | 7.9 |
| C38 | 1.6 | 0.1 | 5.6 | 2.1 | 1.5 | 4.7 | 81.6 | 3.6 | 8.2 |
| C39 | 1.6 | 0.1 | 6.7 | 2.1 | 1.6 | 4.5 | 81.4 | 3.7 | 9.2 |
| C40 | 1.9 | 0.2 | 7.7 | 2.1 | 1.5 | 4.1 | 81.5 | 3.6 | 10.1 |
| C41 | 2.1 | 0.1 | 12.8 | 2.4 | 1.7 | 4.2 | 76.0 | 4.2 | 15.5 |
| C42 | 2.6 | 0.0 | 15.0 | 4.3 | 3.1 | 4.5 | 69.0 | 7.4 | 18.5 |
| C43 | 1.8 | 0.1 | 11.3 | 2.3 | 1.7 | 4.3 | 78.4 | 3.9 | 13.8 |
| C44 | 2.0 | 0.1 | 9.5 | 2.5 | 1.9 | 4.3 | 79.1 | 4.4 | 12.9 |
| C45 | 1.6 | 0.1 | 7.2 | 2.1 | 1.6 | 4.2 | 79.4 | 3.7 | 9.7 |
| C46 | 1.7 | 0.0 | 8.8 | 2.1 | 1.5 | 3.9 | 81.2 | 3.6 | 11.2 |
| C47 | 1.6 | 0.1 | 8.6 | 2.2 | 1.6 | 4.2 | 82.8 | 3.8 | 11.0 |
| C48 | 2.0 | 0.1 | 10.1 | 2.5 | 1.9 | 4.2 | 78.2 | 4.4 | 12.9 |
| C49 | 1.8 | 0.0 | 6.4 | 2.3 | 1.6 | 3.8 | 81.9 | 3.9 | 9.0 |

TABLE 19

Selectivities of the products obtained in the catalyst tests
Selectivities (%)

| Catalyst | Calcination temp (° C.) | Flow rate or air (ml/mn/gca) | Oven temperature (° C.) | Hot temp. (° C.) | TTG = total TTU | TTG O$_2$ = total TTU | C balance | O balance | Acetaldehyde |
|---|---|---|---|---|---|---|---|---|---|
| C33 | 280 | 0 | 400 | 412 | 16.5 | 35.0 | 98.4 | 102.1 | 0.0 |
| C34 | 280 | 10.6 | 400 | 411 | 15.6 | 31.6 | 98.8 | 103.2 | 0.1 |

TABLE 19-continued

Selectivities of the products obtained in the catalyst tests
Selectivities (%)

| Catalyst | | | | | | | | | |
|---|---|---|---|---|---|---|---|---|---|
| C35 | 290 | 0 | 400 | 412 | 16.5 | 34.5 | 99.3 | 103.0 | 0.1 |
| C36 | 290 | 10.6 | 400 | 411 | 15.5 | 30.9 | 98.2 | 102.1 | 0.0 |
| C37 | 300 | 0 | 400 | 410 | 14.4 | 28.1 | 99.6 | 98.1 | 0.0 |
| C38 | 300 | 10 | 400 | 411 | 15.7 | 32.2 | 97.3 | 97.5 | 0.0 |
| C39 | 300 | 20.1 | 400 | 413 | 16.7 | 34.4 | 98.1 | 101.6 | 0.0 |
| C40 | 300 | 51.6 | 400 | 405 | 17.7 | 36.5 | 99.3 | 99.6 | 0.0 |
| C41 | 320 | 0 | 400 | 414 | 23.5 | 48.7 | 99.5 | 103.1 | 0.0 |
| C42 | 320 | 0 | 420 | 438 | 29.6 | 67.3 | 98.7 | 101.6 | 0.0 |
| C43 | 320 | 10 | 400 | 414 | 21.6 | 44.2 | 100.0 | 102.5 | 0.0 |
| C44 | 280 | 21.2 | 400 | 413 | 20.5 | 45.6 | 99.5 | 101.8 | 0.0 |
| C45 | 290 | 19.1 | 400 | 414 | 16.9 | 35.7 | 96.3 | 95.8 | 0.1 |
| C46 | 320 | 19.2 | 400 | 413 | 18.1 | 39.4 | 99.2 | 95.7 | 0.0 |
| C47 | 280 | 49.2 | 400 | 415 | 18.3 | 39.8 | 101.1 | 99.9 | 0.0 |
| C48 | 290 | 52.9 | 400 | 414 | 20.9 | 46.7 | 99.1 | 101.8 | 0.0 |
| C49 | 320 | 51.6 | 400 | 412 | 16.1 | 36.2 | 98.0 | 99.1 | 0.1 |

| Catalyst | Propanaldehyde | Acetone | Acrolein | Allyl alcohol | Allyl acrylate | Acetic acid | Propionic acid | Acrylic acid | CO | $CO_2$ | Propene |
|---|---|---|---|---|---|---|---|---|---|---|---|
| C33 | 0.0 | 0.7 | 0.1 | 0.0 | 0.0 | 11.5 | 0.3 | 32.2 | 15.7 | 11.6 | 27.8 |
| C34 | 0.0 | 0.9 | 0.1 | 0.0 | 0.0 | 9.7 | 0.3 | 37.2 | 13.1 | 9.8 | 28.8 |
| C35 | 0.0 | 0.7 | 0.1 | 0.0 | 0.0 | 10.5 | 0.3 | 34.8 | 14.6 | 11.0 | 27.9 |
| C36 | 0.0 | 0.9 | 0.1 | 0.0 | 0.0 | 9.6 | 0.3 | 38.6 | 12.8 | 8.9 | 28.9 |
| C37 | 0.0 | 0.8 | 0.4 | 0.0 | 0.0 | 8.5 | 0.7 | 38.0 | 11.7 | 8.7 | 31.1 |
| C38 | 0.0 | 0.9 | 0.2 | 0.0 | 0.0 | 10.3 | 0.4 | 35.4 | 13.4 | 9.8 | 29.7 |
| C39 | 0.0 | 0.9 | 0.1 | 0.0 | 0.0 | 9.7 | 0.4 | 39.9 | 12.6 | 9.3 | 27.0 |
| C40 | 0.0 | 1.6 | 0.0 | 0.0 | 0.0 | 10.7 | 1.0 | 43.2 | 11.6 | 8.5 | 23.4 |
| C41 | 0.0 | 0.8 | 0.1 | 0.0 | 0.0 | 8.8 | 0.3 | 54.5 | 10.4 | 7.3 | 17.9 |
| C42 | 0.0 | 0.4 | 0.1 | 0.0 | 0.0 | 8.7 | 0.1 | 50.6 | 14.5 | 10.6 | 15.1 |
| C43 | 0.0 | 0.7 | 0.1 | 0.0 | 0.0 | 8.5 | 0.3 | 52.3 | 10.5 | 7.7 | 20.0 |
| C44 | 0.0 | 0.8 | 0.1 | 0.0 | 0.0 | 9.7 | 0.3 | 46.6 | 12.4 | 9.2 | 20.9 |
| C45 | 0.0 | 0.2 | 0.1 | 0.0 | 0.0 | 9.7 | 0.3 | 42.8 | 12.5 | 9.6 | 24.7 |
| C46 | 0.0 | 0.3 | 0.1 | 0.0 | 0.0 | 9.5 | 0.3 | 48.4 | 11.5 | 8.3 | 21.7 |
| C47 | 0.0 | 0.3 | 0.1 | 0.0 | 0.0 | 9.0 | 0.3 | 46.9 | 11.9 | 8.7 | 22.9 |
| C48 | 0.0 | 0.3 | 0.1 | 0.0 | 0.0 | 9.5 | 0.3 | 48.3 | 11.9 | 9.3 | 20.3 |
| C49 | 0.0 | 0.2 | 0.1 | 0.0 | 0.0 | 11.5 | 0.2 | 39.9 | 14.4 | 10.1 | 23.6 |

It is therefore seen that the best results are obtained with a precalcination at 320° C. and under a zero flow rate of air, followed by a calcination at 600° C. for 2 hours under a flow rate of nitrogen of 50 ml/mn/g.

The invention claimed is:

1. Process for the production of acrylic acid from propane, wherein a gaseous mixture comprising propane, water vapor, and optionally an inert gas,
   either in the absence of oxygen,
   or in the presence of molecular oxygen, wherein when operating in the presence of molecular oxygen the molar ratio propane/molecular oxygen in the initial gaseous mixture is greater than or equal to 0.5;
   is passed over a catalyst of formula (I):

$$Mo_1V_aSb_bNb_cSi_dO_x \quad (I)$$

in which:
   a is between 0.006 and 1, inclusive;
   b is between 0.006 and 1, inclusive;
   c is between 0.006 and 1, inclusive;
   d is between 0 and 3.5, inclusive; and
   x is the quantity of oxygen bound to the other elements and depends on their oxidation state,
in order to oxidize the propane to acrylic acid.

2. Process according to claim 1, in which the molar proportions of the constituents of the initial gaseous mixture are as follows:

propane/$O_2$/inert gas/$H_2O$ (vapor)=1/0.05-2/1-10/1-10.

3. Process according to claim 1, in which the molar proportions of the constituents of the initial gaseous mixture are as follows:

propane/$O_2$/inert gas/$H_2O$ (vapor)=1/0.1-1/1-5/1-5.

4. Process according to claim 1, in which, in the catalyst of formula (i):
   a is between 0.09 and 0.8, inclusive;
   b is between 0.04 and 0.6, inclusive;
   c is between 0.01 and 0.4, inclusive; and
   d is between 0.4 and 1.6, inclusive.

5. Process according to claim 1, wherein the oxidation reactions are carried out at a temperature of 200 to 500° C.

6. Process according to claim 1, wherein the oxidation reaction is carried out at a temperature of 250 to 450° C.

7. Process according to claim 1, wherein the oxidation reactions are carried out at a pressure of $1.01 \times 10^4$ to $1.01 \times 10^6$ Pa (0.1 to 10 atmospheres).

8. Process according to claim 1, wherein the oxidation reactions are carried out at a pressure of $5.05 \times 10^4$ to $5.05 \times 10^5$ Pa (0.5-5 atmospheres).

9. Process according to claim 1, which is used until there is a reduction ratio of the catalyst comprised between 0.1 and 10 g of oxygen per kg of catalyst.

10. Process according to claim 1, wherein once the catalyst has at least partially changed to the reduced state, its regeneration is carried out according to reaction (C):

$$SOLID_{reduced} + O_2 \rightarrow SOLID_{oxidized} \quad (C)$$

by heating in the presence of oxygen or a gas containing oxygen at a temperature of 250 to 500° C., for a period necessary for the reoxidation of the catalyst.

11. Process according to claim 10, wherein the oxidation and the regeneration (C) reactions are carried out in a device with two stages, namely a reactor and a regenerator which operate simultaneously and in which two catalyst loads alternate periodically.

12. Process according to claim 10, wherein the oxidation and the regeneration (C) reactions are carried out in the same reactor alternating the periods of reaction and regeneration.

13. Process according to claim 10, wherein the oxidation and the regeneration (C) reactions are carried out in a reactor with a moving bed.

14. Process according to claim 1, in which:
a) the initial gaseous mixture is introduced into a first reactor with a moving catalyst bed,
b) at an outlet of the first reactor, the gaseous mixture is separated from the catalyst;
c) the catalyst is returned into a regenerator;
d) optionally, the gaseous mixture is introduced into a second reactor with a moving catalyst bed;
e) if the gases are introduced into a second reactor with a moving catalyst bed, at an outlet of the second reactor, the are gaseous mixture is separated from the catalyst and the acrylic acid contained in the separated gaseous mixture is recovered;
f) if the gases are introduced into a second reactor with a moving catalyst bed, the catalyst of the second reactor is returned into the regenerator; and
g) regenerated catalyst from the regenerator is reintroduced into the first reactor and, if the gases are introduced into a second reactor with a moving catalyst bed, into the second reactor.

15. Process according to claim 14, in which the first and second reactors are vertical and the catalyst is moved upwards by the gas flow.

16. Process according to claim 1, wherein the oxidation reactions are carried out with a residence time of 0.01 to 90 seconds in each reactor.

17. Process according to claim 1, wherein the oxidation reactions are carried out with a residence time of 0.1 to 30 seconds.

18. Process according to claim 1, wherein propylene produced or the propane which has not reacted or both are recycled to an inlet of a reactor, or if there are several reactors, to an inlet of a first reactor.

19. Process according to claim 1, in which a reactor, or when there are several reactors, at least one of the reactors, also comprises a cocatalyst corresponding to the following formula (II):

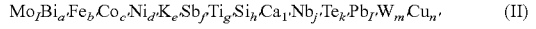

in which:
a' is between 0.006 and 1, inclusive
b' is between 0 and 3.5, inclusive;
c' is between 0 and 3.5, inclusive;
d' is between 0 and 3.5, inclusive;
e' is between 0 and 1, inclusive;
f' is between 0 and 1, inclusive;
g' is between 0 and 1, inclusive;
h' is between 0 and 3.5, inclusive;
i' is between 0 and 1, inclusive;
j' is between 0 and 1, inclusive;
k' is between 0 and 1, inclusive;
l' is between 0 and 1, inclusive;
m' is between 0 and 1, inclusive; and
n' is between 0 and 1, inclusive.

20. Process according to claim 19, in which the cocatalyst is regenerated and circulates in the same way as the catalyst.

21. Process according to claim 19, in which, in the cocatalyst of formula (II):
a' is between 0.01 and 0.4, inclusive;
b' is between 0.2 and 1.6, inclusive;
c' is between 0.3 and 1.6, inclusive;
d' is between 0.1 and 0.6, inclusive;
e' is between 0.006 and 0.01, inclusive;
f' is between 0 and 0.4, inclusive;
g' is between 0 and 0.4, inclusive;
h' is between 0.01 and 1.6, inclusive
i' is between 0 and 0.4, inclusive;
j' is between 0 and 0.4, inclusive;
k' is between 0 and 0.4, inclusive;
l' is between 0 and 0.4, inclusive;
m' is between 0 and 0.4, inclusive; and
n' is between 0 and 0.4, inclusive.

22. Process according to claim 19, in which, a weight ratio of the catalyst to the cocatalyst greater than 0.5 is used.

23. Process according to claim 19, in which, a weight ratio of the catalyst to the cocatalyst of at least 1 is used.

24. Process according to claim 19, in which the catalyst and the cocatalyst are mixed.

25. Process according to claim 19, in which the catalyst and the cocatalyst are present in the form of pellets, each pellet comprising both the catalyst and the cocatalyst.

26. Process according to claim 1, comprising the repetition, in a reactor provided with the catalyst of formula (I) defined in claim 1, and, or the cocatalyst of formula (II) defined in claim 19, of the cycle comprising the following successive stages:
1) a stage of injection of the gaseous mixture as defined in claim 1;
2) a stage of injection of water vapor and, if appropriate, inert gas;
3) a stage of injection of a mixture of molecular oxygen, water vapor and, optionally, inert gas; and
4) a stage of injection of water vapor and, optionally, inert gas.

27. Process according to claim 26, wherein the cycle comprises an additional stage which precedes or follows stage 1) and during which a gaseous mixture corresponding to that of stage 1) but without molecular oxygen is injected, the molar ratio propane/molecular oxygen then being calculated globally for stage 1) and this additional stage.

28. Process according to claim 27, wherein the additional stage precedes stage I) in the cycle.

29. Process according to claim 26, wherein the reactor is a reactor with a moving bed.

30. Process for the production of acrylic acid from propane, wherein a gaseous mixture comprising propane, water vapor, and optionally an inert gas,
either in the absence of oxygen,
or in the presence of molecular oxygen, wherein when operating in the presence of molecular oxygen the molar ratio propane/molecular oxygen in the initial gaseous mixture is greater than or equal to 0.5; is passed over a catalyst of formula (I):

in which:
a is between 0.006 and 1, inclusive;
b is between 0.006 and 1, inclusive;
c is between 0.006 and 1, inclusive;
d is between 0 and 3.5, inclusive; and
x is the quantity of oxygen bound to the other elements and depends on their oxidation state,
in order to oxidize the propane to acrylic acid, and in which:

a) the initial gaseous mixture is introduced into a first reactor with a moving catalyst bed, b) at an outlet of the first reactor, gases are separated from the catalyst;

c) the catalyst is returned into a regenerator;

d) optionally, the gases are introduced into a second reactor with a moving catalyst bed;

e) if the gases are introduced into a second reactor with a moving catalyst bed, at an outlet of the second reactor, the gases are separated from the catalyst and the acrylic acid contained in the separated gases is recovered;

f) if the gases are introduced into a second reactor with a moving catalyst bed, the catalyst of the second reactor is returned into the regenerator; and g) regenerated catalyst from the regenerator is reintroduced into the first reactor and, if the gases are introduced into a second reactor with a moving catalyst bed, into the second reactor.

31. Process according to claim 30, in which the molar proportions of the constituents of the initial gaseous mixture are as follows:

propane/O$_2$/inert gas/H$_2$O(vapor)=1/0.05-2/1-10/1-10.

32. Process according to claim 30, in which, in the catalyst of formula (I):

a is between 0.09 and 0.8, inclusive;
b is between 0.04 and 0.6, inclusive;
c is between 0.01 and 0.4, inclusive; and
d is between 0.4 and 1.6, inclusive.

33. Process for the production of acrylic acid from propane, wherein a gaseous mixture comprising propane, water vapor, and optionally an inert gas, either in the absence of oxygen, or in the presence of molecular oxygen, wherein when operating in the presence of molecular oxygen the molar ratio propane/molecular oxygen in the initial gaseous mixture is greater than or equal to 0.5;

is passed over a catalyst of formula (I):

$$Mo_1V_aSb_bNb_cSi_dO_x \qquad (I)$$

in which:

a is between 0.006 and 1, inclusive;
b is between 0.006 and 1, inclusive;
c is between 0.006 and 1, inclusive;
d is between 0 and 3.5, inclusive; and
x is the quantity of oxygen bound to the other elements and depends on their oxidation state, in order to oxidize the propane to acrylic acid, comprising repetition, in a reactor provided with the catalyst of formula (I) above, of a cycle comprising the following successive stages:

1) a stage of injection of the gaseous mixture as defined above;

2) a stage of injection of water vapor and, optionally, inert gas;

3) a stage of injection of a mixture of molecular oxygen, water vapor and, optionally, inert gas; and 4) a stage of injection of water vapor and, if appropriate, inert gas.

34. Process according to claim 33, in which, in the catalyst of formula (I):

a is between 0.09 and 0.8, inclusive;
b is between 0.04 and 0.6, inclusive;
c is between 0.01 and 0.4, inclusive; and
d is between 0.4 and 1.6, inclusive.

35. Process according to claim 33, wherein the cycle comprises an additional stage which precedes or follows stage 1) and during which a gaseous mixture corresponding to that of stage 1) but without molecular oxygen is injected, the molar ratio propane/molecular oxygen then being calculated globally for stage 1) and this additional stage.

36. Process according to claim 33, wherein the additional stage precedes stage I) in the cycle.

* * * * *